(12) United States Patent
Aran et al.

(10) Patent No.: US 10,729,895 B2
(45) Date of Patent: Aug. 4, 2020

(54) ACTIVE AGENT DELIVERY DEVICES AND METHODS OF USING THE SAME

(71) Applicant: The Regents of the University of California, Oakland, CA (US)

(72) Inventors: Kiana Aran, Berkeley, CA (US); Jacobo Paredes, Berkeley, CA (US); Niren Murthy, Berkeley, CA (US); Dorian Liepmann, Lafayette, CA (US); Kunwoo Lee, Albany, CA (US)

(73) Assignee: The Regents of the University of California, Oakland, CA (US)

( * ) Notice: Subject to any disclaimer, the term of this patent is extended or adjusted under 35 U.S.C. 154(b) by 18 days.

(21) Appl. No.: 15/513,110

(22) PCT Filed: Sep. 29, 2015

(86) PCT No.: PCT/US2015/052901
§ 371 (c)(1),
(2) Date: Mar. 21, 2017

(87) PCT Pub. No.: WO2016/054015
PCT Pub. Date: Apr. 7, 2016

(65) Prior Publication Data
US 2017/0246438 A1 Aug. 31, 2017

Related U.S. Application Data

(60) Provisional application No. 62/057,887, filed on Sep. 30, 2014.

(51) Int. Cl.
*A61M 31/00* (2006.01)
*A61K 9/00* (2006.01)
*A61K 39/00* (2006.01)

(52) U.S. Cl.
CPC ........... *A61M 31/002* (2013.01); *A61K 9/006* (2013.01); *A61K 39/0005* (2013.01); *A61M 31/00* (2013.01); *A61K 2039/542* (2013.01); *A61M 2202/064* (2013.01); *A61M 2205/3324* (2013.01); *A61M 2205/3334* (2013.01); *A61M 2205/36* (2013.01)

(58) Field of Classification Search
CPC . A61M 31/002; A61K 9/006; A61K 39/0005; A61K 2039/542
USPC ........................................................ 604/890.1
See application file for complete search history.

(56) References Cited

U.S. PATENT DOCUMENTS

| | | | |
|---|---|---|---|
| 4,573,447 A | | 3/1986 | Thrash et al. |
| 5,858,001 A | * | 1/1999 | Tsals ................. A61M 5/14248 604/135 |

(Continued)

FOREIGN PATENT DOCUMENTS

EP    0108607    5/1984

*Primary Examiner* — Phillip A Gray
(74) *Attorney, Agent, or Firm* — Rudy J. Ng; Bozicevic, Field & Francis LLP

(57) ABSTRACT

Provided are active agent delivery devices configured to deliver an active agent formulation into or through a mucosal layer in a subject. The active agent delivery devices include a power reservoir configured to eject the active agent formulation at a pressure sufficient to deliver the active agent formulation into or through a mucosal layer in a subject. Methods of using the subject active agent delivery devices are also provided.

29 Claims, 15 Drawing Sheets

(56) References Cited

U.S. PATENT DOCUMENTS

| | | | | |
|---|---|---|---|---|
| 5,891,097 A | * | 4/1999 | Saito | A61M 5/1483 604/131 |
| 2002/0156461 A1 | * | 10/2002 | Joshi | A61M 5/14244 604/891.1 |
| 2005/0010168 A1 | * | 1/2005 | Kendall | A61M 5/3015 604/70 |
| 2007/0043320 A1 | * | 2/2007 | Kenany | A61M 37/00 604/68 |
| 2011/0313348 A1 | * | 12/2011 | Potter | A61M 5/30 604/60 |

* cited by examiner

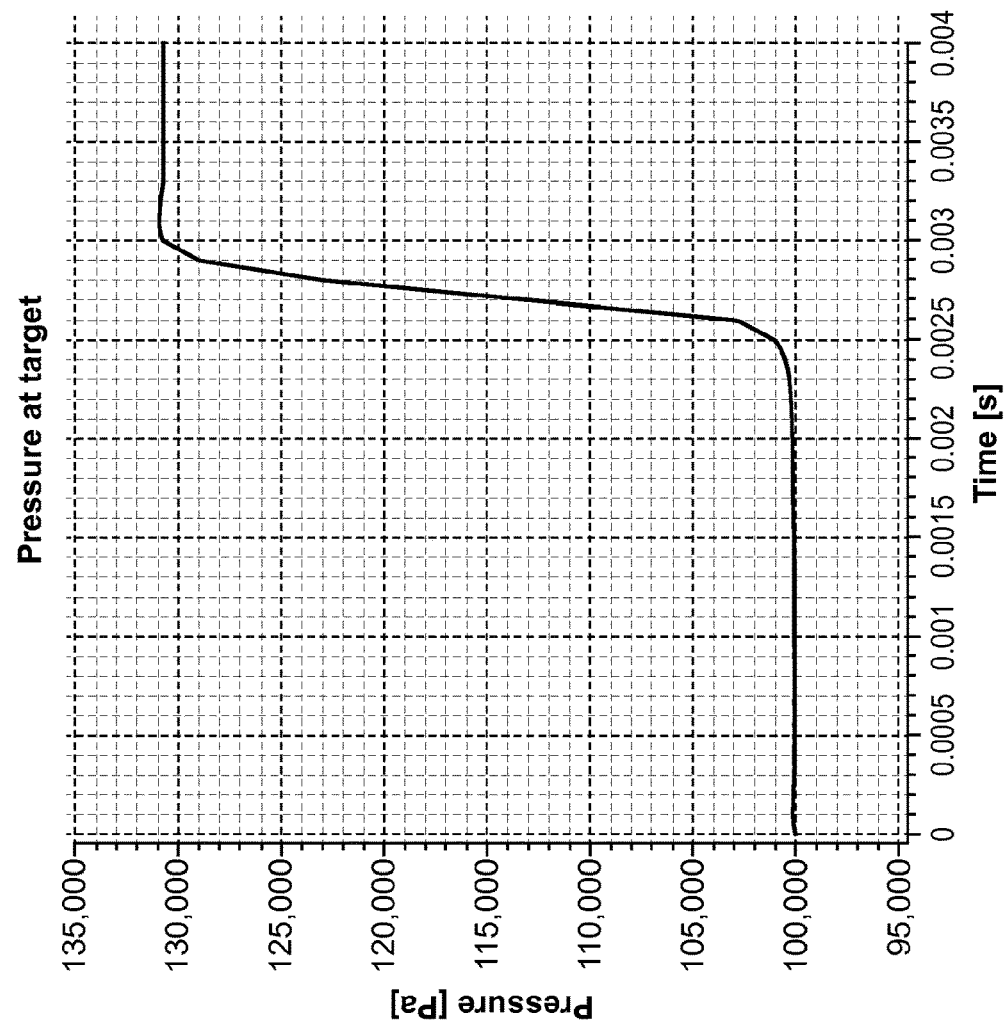
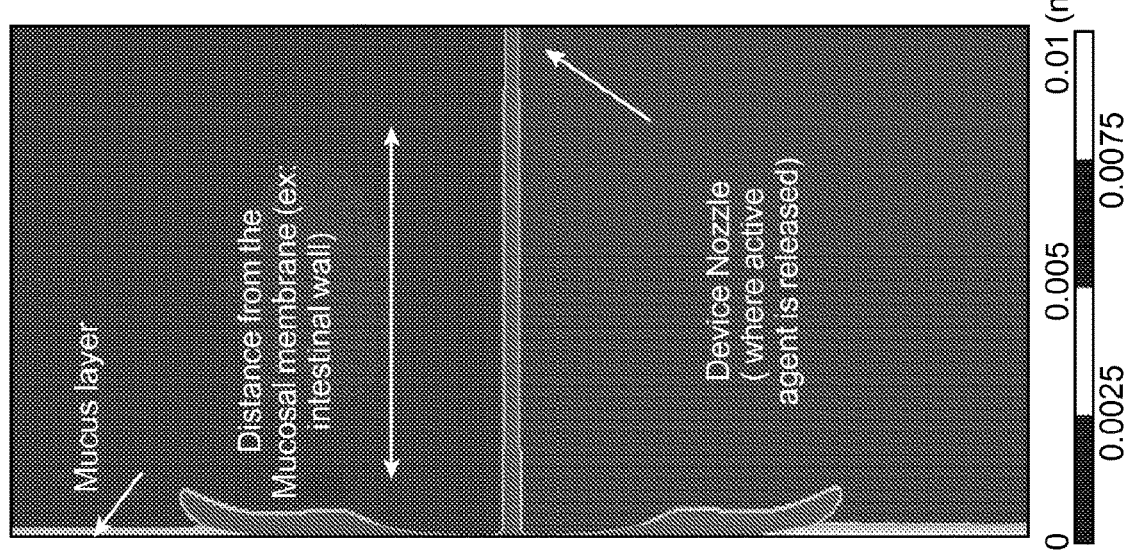
FIG. 5A
FIG. 5B

FIG. 7

Buccal Transmucosal Delievery of Ovalbumin
(*in-vitro* pig tissue studies)

A Buccal delivery with active agent delivery device
B Buccal delivery without active agent delivery device

ACTIVE AGENT DELIVERY DEVICES AND METHODS OF USING THE SAME

CROSS-REFERENCE TO RELATED APPLICATION

This application claims priority under 35 U.S.C. § 119(e) to the filing date of U.S. Provisional Application No. 62/057,887, filed Sep. 30, 2014, the disclosure of which is incorporated herein by reference.

REFERENCE TO GOVERNMENT SUPPORT

This invention was made with government support under grant numbers HHSN268201000043C and HL096796 awarded by the National Institutes of Health. The government has certain rights in the invention.

INTRODUCTION

The effort to develop needle-free active agent delivery systems through the non-invasive transmucosal route including but not limited to buccal, endosinusial, endotracheal, enteral, intragastric, transtracheal, auricular, intraocular, retrobulbar, conjunctival, vaginal, urogenital, anal and nasal has been a challenge due to the poor mucus permeability, leading to low active agent bioavailability and therapeutic efficacy. The low active agent bioavailability in the transmucosal route is mainly due to the physical and biochemical barrier to absorption of the active agent, such as large molecules including proteins and peptides, that is formed by the mucosal layer. Over the past decades several technologies have been explored to overcome the mucus biochemical barrier, such as by developing nanoparticles and liposomes to minimize enzymatic degradation, and by attempting to increase active agent absorption through the mucus physical barrier at the site of active agent release by developing mucoadhesives and absorption enhancers. Despite these efforts over the past decades, non-invasive mucosal delivery remains a challenge. Thus, there is a need for a suitable delivery system for administering active agents that can maintain the active agent integrity, improve bioavailability and overcome the mucus barrier to facilitate active agent absorption at the site where the active agent is released.

SUMMARY

The present disclosure provides active agent delivery devices, which can deliver a high-pressure jet of an active agent formulation into and/or through mucosal membranes in a subject. The high-pressure delivery of the active agent formulation can provide for an increased diffusion rate across the mucosal barrier, which can maximize active agent absorption into the cells in the mucosal layer and/or deliver the active agent to the systemic circulation. Embodiments of the devices of the present disclosure include at least two reservoirs, a power reservoir and an active agent reservoir, separated by a movable separator. In certain embodiments, the device utilizes vaporization energy to apply a force to the movable separator, which propels the active agent formulation at a high velocity to facilitate penetration of the active agent into the mucosal layer and thus facilitate a maximization in mucosal absorption. Accordingly, the active agent delivery devices may include any pressure generating element in the power reservoir for mucosal and/or transmucosal active agent delivery, including, but not limited to, pressure-generating ingestible devices, pressure-generating sublingual devices, pressure-generating buccal devices, pressure-generating vaginal devices, pressure-generating nasal devices, pressure-generating ocular devices, and the like.

Aspects of the active agent delivery devices include an enclosure that houses a power reservoir configured to produce a pressure sufficient to deliver the active agent formulation into and/or through a mucosal layer in a subject. Also provided are methods of using the device, e.g., to deliver an active agent to a human or animal subject, as well as kits that include the device, e.g., a sealed packaging or container having one or more of the devices.

The penetrative process of the active agent ejection from the device may depend on various factors, such as, but not limited to, the device geometry, the size and number of the nozzles for active agent release, the amount of active agent to be delivered, the viscosity and chemical properties of the active agent or active agent formulation to be delivered, the mucus thickness at the site of delivery, and the intended target layer of the active agent. Devices of the present disclosure can be configured to deliver any desired active agent into and/or through a mucosal layer in a subject. In certain embodiments, a pretreatment may be used on the mucosal layer that changes the morphology and properties of the mucosal layer to enhance the bioavailability and increase the extent of active agent penetration into the mucosal layer. In certain embodiments, the pressure produced by the power reservoir and the active agent penetration depth of the device can be adjusted by changing, for example, the amount or type of pressure generating material in the power reservoir, the dimensions of the device, the number and/or size of the active agent delivery nozzles, which can enhance mucosal and/or transmucosal adsorption of the active agent.

In certain embodiments, the pressure produced by the active agent delivery device can cause mucous removal and/or decreased mucosal thickness when the ejected active agent formulation contacts the mucosal layer. In some cases, the mucosal immune system (which is immediately below the mucous barrier) is exposed by the mucous removal and/or decreased mucosal thickness. In certain instances, active agent delivery to the mucosal immune system can be used for delivering active agents (e.g., vaccine active agents) that provoke an immune response, both systemic (IgG) as well as local (secretory IgA (sIgA) at the mucosa). Delivery of vaccine active agents may facilitate targeting pathogens whose route of entry is the mucosa. In addition, because the mucosal immune system is part of the main immune system, delivery of active agents to the mucosal immune system may ameliorate autoimmunity, where the body is either over-reacting to an antigen (e.g., allergies, food intolerance, etc.) or auto-antigen (e.g., multiple sclerosis), or under-reacting to an auto-antigen (e.g., cancer). For example, targeting the mucosal immune system directly may facilitate an increase in the subject's production of an antibody response, and thus may not require subsequent administration of additional vaccine after the initial dose (e.g., a vaccine booster may not be required). In other instances, delivery of an active agent to the mucosal immune system may be useful for desensitization immunotherapy, for example where a subject is desensitized or becomes tolerant to an allergen.

In certain instances, higher pressures may be used to deliver the active agent systemically (e.g., through multiple layers of cells) to the blood. As described herein, the pressure produced by the power reservoir and thus the active agent penetration depth achieved by the device can be increased by changing, for example, the amount or type of pressure generating material in the power reservoir, the dimensions of the device, the number and/or size of the active agent delivery nozzles, which can facilitate delivery of the active agent systemically.

As described herein, targeting strategies may be used to provide for delivery of the active agent to certain target locations in a subject, e.g., intestines, stomach, nasal mucosa, buccal, endosinusial, endotracheal, enteral, intragastric, transtracheal, auricular, intraocular, retrobulbar, conjunctival, vaginal, urogenital, anal, etc.

Accordingly, aspects of the present disclosure include an active agent delivery device that includes: an active agent reservoir at an active agent reservoir end of the device configured to contain an active agent formulation; a power reservoir at a power reservoir end of the device configured to eject the active agent formulation at a pressure sufficient to deliver the active agent formulation into or through a mucosal layer in a subject; and a moveable separator separating the power reservoir from the active agent reservoir.

In some embodiments, the pressure generated by the device is 30 kPa or more.

In some embodiments, the active agent formulation is ejected from the device in 10 msec or less.

In some embodiments, the active agent formulation is ejected from the device at a velocity of 1 m/s or more.

In some embodiments, the device includes a nozzle separating the active agent reservoir from the exterior of the device.

In some embodiments, the power reservoir contains a gas generating material.

In some embodiments, the gas generating material produces a gas upon contact with an aqueous medium.

In some embodiments, the gas is a product of a chemical reaction.

In some embodiments, the gas generating material is a volatile liquid.

In some embodiments, the volatile liquid has a vaporization temperature ranging from 37.5° C. to 45° C.

In some embodiments, the gas generating material is present in the moveable separator.

In some embodiments, the device includes a heat reservoir in heat transfer relationship with the power reservoir, where the heat reservoir includes a heat generating material that produces heat upon contact with an aqueous medium.

In some embodiments, the device includes a valve separating the power reservoir from the exterior of the device.

In some embodiments, the valve includes a pH responsive material.

In some embodiments, the pH responsive material includes a polymer.

In some embodiments, the device further includes an aqueous medium reservoir configured to contact at least a portion of the power reservoir end of the device and activate the power reservoir.

In some embodiments, the power reservoir contains a gas generating material and the aqueous medium reservoir contains an aqueous medium.

In some embodiments, the active agent includes a macromolecule.

In some embodiments, the macromolecule includes a protein.

In some embodiments, the active agent formulation includes a liquid.

In some embodiments, the device includes a tubular member having a planar surface at the active agent reservoir end and a hemispherical structure at the power reservoir end.

In some embodiments, the device is configured to promote contact of the active agent reservoir end with a mucosal surface in a subject.

Aspects of the present disclosure include a method of delivering an active agent to a subject. The method includes administering an active agent delivery device of the present disclosure to a subject.

In some embodiments, the method is a method of treating the subject for a disease condition.

Aspects of the present disclosure include a kit. The kit includes an active agent delivery device of the present disclosure and a packaging containing the active agent delivery device.

In some embodiments, the packaging contains two or more active agent delivery devices of the present disclosure.

In some embodiments, the kit includes a mucosal treatment agent

BRIEF DESCRIPTION OF THE FIGURES

FIG. 5A shows an image from a simulation study to evaluate the effect of pressure on penetration depth through the intestinal wall using a device of the present disclosure. FIG. 5B provides a graph of the results of simulation studies to predict the effect of pressure in enhancing the active agent penetration into mucosal membranes in the small intestine, according to embodiments of the present disclosure.

FIG. 7 provides a graph of the in vitro results from buccal transmucosal ovalbumin delivery with and without using a device of the present disclosure in fresh pig buccal tissue.

Figure 1:
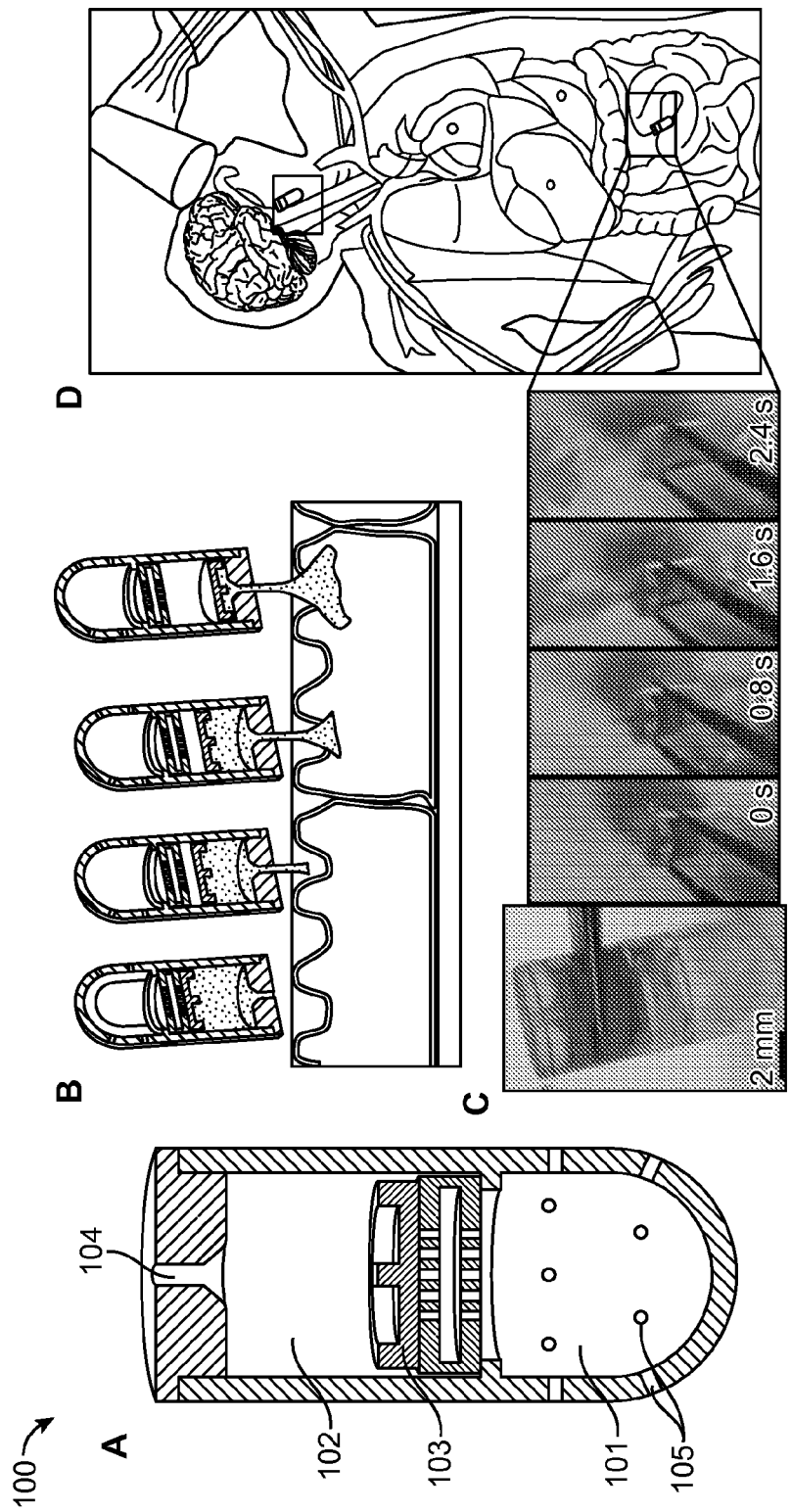
FIG. 1 provides views of an active agent delivery device where the device is activated by a gas generating chemical reaction, according to embodiments of the present disclosure.

Before the present invention is described in greater detail, it is to be understood that aspects of the present disclosure are not limited to the particular embodiments described, and as such may, of course, vary. It is also to be understood that the terminology used herein is for the purpose of describing particular embodiments only, and is not intended to be limiting, since the scope of embodiments of the present disclosure will be defined only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges and are also encompassed within embodiments of the present disclosure, subject to any specifically excluded limit in the stated range. Where the stated range includes one or both of the limits ranges excluding either or both of those included limits are also included in embodiments of the present disclosure. In addition it is understood that the invention can be in the form of an ingestible pill, patch and any form of a device that can be administered or placed close to mucosal membranes as described in this document are also included in embodiments of the present disclosure Unless defined otherwise, all technical and scientific terms used herein have the same meaning as commonly understood by one of ordinary skill in the art to which this invention belongs. Although any methods and materials similar or equivalent to those described herein can also be used in the practice or testing of embodiments of the present disclosure, representative illustrative methods and materials are now described. All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that embodiments of the present disclosure are not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

DETAILED DESCRIPTION

Active Agent Delivery Devices

Provided are active agent delivery devices configured to deliver an active agent formulation into and/or through a mucosal layer in a subject (e.g., mucosal and/or transmucosal active agent delivery devices). The active agent delivery devices include a power reservoir configured to eject the active agent formulation at a pressure sufficient to deliver the active agent formulation into or through a mucosal layer in a subject. For example, the active agent delivery devices may deliver an active agent formulation into the mucosal layer in the subject, such as by delivering the active agent formulation through the surface of the mucosal layer into the interior of the mucosal layer in the subject. In other instances, the active agent delivery devices deliver the active agent formulation through the mucosal layer in the subject, such as by delivering the active agent formulation through the thickness of the mucosal layer and to the underlying tissues in the subject. In some cases, the active agent delivery devices deliver the active agent formulation into and/or through the mucosal layer, such that the active agent is delivered to the mucosal immune system in the subject.

Accordingly, active agent delivery devices of the present disclosure may be configured to produce a sufficiently high pressure in the power reservoir to propel the active agent formulation out of the device with sufficient velocity to penetrate the surface of the mucosal layer in the subject. In some embodiments, the active agent delivery device is configured to produce a sufficiently high pressure, such that at least a portion of the active agent formulation penetrates the surface of the mucosal layer and delivers the active agent into the mucosal layer in the subject. In some embodiments, the active agent delivery device is configured to produce a sufficiently high pressure, such that at least a portion of the active agent formulation penetrates through the mucosal layer and delivers the active agent through the mucosal layer in the subject (i.e., transmucosal delivery of the active agent). In certain instances, the active agent delivery device is configured to produce a sufficiently high pressure, such that at least a portion of the active agent formulation penetrates through the surface of the mucosal layer and delivers the active agent to the mucosal immune system in the subject.

As summarized above, the active agent delivery devices are designed to deliver the active agents into and/or across mucosal membranes in a subject. By "mucosal delivery" and "transmucosal delivery" is meant that the devices are configured, e.g., dimensioned, to be placed close to and/or in contact with a mucosal membrane of a subject and deliver an active agent into the mucosal membrane (mucosal delivery) and/or through the mucosal membrane (transmucosal delivery). By mucosal membrane is meant any mucosal layer in a subject, such as, but not limited to, buccal, endosinusial, endotracheal, enteral, intragastric, transtracheal, auricular, intraocular, retrobulbar, conjunctival, vaginal, urogenital, anal and nasal. Subjects suitable for delivery of an active agent using a device described herein include human or animal subjects.

To produce a sufficient pressure to deliver an active agent into and/or through a mucosal layer in a subject, the active agent delivery device includes a power reservoir. In addition, the device includes an active agent reservoir. The power reservoir may be positioned at a power reservoir end of the device, and the active agent reservoir may be positioned at an active agent reservoir end of the device. In certain embodiments, the active agent reservoir and the power reservoir are positioned at opposing ends of the device. The power reservoir and the active agent reservoir may be provided in an enclosure that contains the power reservoir and active agent reservoir. In some instances, the enclosure is configured to form one or more side walls of the power reservoir and/or active agent reservoir.

In certain embodiments, the active agent delivery device includes a movable separator (also referred to herein as a piston) that separates the power reservoir from the active agent reservoir. As such, the movable separator is positioned between the power reservoir and the active agent reservoir. In some cases, the movable separator is configured to move inside of the enclosure, such as move in a direction towards the active agent reservoir when a pressure is applied to the movable separator from the power reservoir. For example, the movable separator may move into the active agent reservoir and force the active agent formulation out of the active agent reservoir when a pressure is applied to the movable separator from the power reservoir. The movable separator can be shaped such that the side walls of the movable separator are in contact with the interior walls of the device to minimize contact of the pressure generating material in the power reservoir with the active agent formulation in the active agent reservoir. In some cases, a gap or void may be present between the movable separator and the power reservoir, which may facilitate a minimization in contact between the pressure generating material in the power reservoir and the active agent formulation in the active agent reservoir.

Any form of pressure generating materials or devices can be used in the active agent delivery devices of the present disclosure to produce a sufficiently high pressure to deliver the active agent into and/or through a mucosal layer in the subject. For example, in the power reservoir, pressure can be generated from an electro-mechanical device or mechanism, such as a solenoid or a piezoelectric device, or a pressure generating reaction, such as a gas generating chemical reaction using a gas generating material or a gas generating phase transition using a volatile liquid, combinations thereof, and the like. In certain embodiments, the active agent delivery device is self-contained. By "self-contained" is meant that the device can be activated to deliver the active agent without providing an external pressure source or using an external pressure generating material or device after the device is administered to the subject. For example, as described herein, the device includes a power reservoir configured to produce a pressure sufficient to deliver the active agent formulation into and/or through the mucosal layer in the subject.

Examples of pressure generating materials that can be used in the active agent delivery device include, but are not limited to a gas generating material, such as a gas generating material that produces a gas upon contact with an aqueous medium (e.g., water). For example, the gas generating material can be a mixture of citric acid and sodium bicarbonate. When the gas generating material contacts an aqueous medium (e.g., water or an aqueous medium contained in a subject, such as an aqueous medium in an intestine, stomach, mouth, vagina, anus, urethra, etc. of a subject), the gas generating material can produce a gas. For instance, when gas generating material (e.g., the mixture of citric acid and sodium bicarbonate) contacts an aqueous medium, a gas generating chemical reaction can occur that produces a gas (e.g., carbon dioxide, $CO_2$). Production of a gas inside the power reservoir of the device can increase the pressure in the power reservoir of the device. When the pressure in the power reservoir reaches a certain threshold pressure, the pressure can force the movable separator between the power reservoir and the active agent reservoir towards the active agent reservoir, thus forcing the active agent out of the active agent reservoir. Pressure generating materials that can be used in the active agent delivery devices should be substantially non-toxic to the subject and should not produce significant amounts of toxic byproducts.

In other embodiments, the pressure generating material that can be used in the active agent delivery device is a gas generating material, such as a gas generating material that produces a gas upon a phase transition of the gas generating material. For example, the gas generating material can be a volatile liquid, such as, but not limited to, an organic solvent (e.g., pentane, hexane, etc.). The volatile liquid may vaporize to produce a gas. As described above, production of a gas inside the power reservoir of the device can increase the pressure in the power reservoir of the device. When the pressure in the power reservoir reaches a certain threshold pressure, the pressure can force the movable separator between the power reservoir and the active agent reservoir towards the active agent reservoir, thus forcing the active agent out of the active agent reservoir. In certain embodiments, the volatile liquid has a vaporization temperature greater than the normal body temperature of the subject. For example, if the subject is a human, the typical body temperature is 37° C., and in these cases the volatile liquid can have a vaporization temperature greater than 37° C., such as 37.5° C. or more, or 38° C. or more, or 38.5° C. or more, or 39° C. or more, or 39.5° C. or more, or 40° C. or more, or 40.5° C. or more, or 41° C. or more, or 41.5° C. or more, or 42° C. or more, or 42.5° C. or more, or 43° C. or more, or 43.5° C. or more, or 44° C. or more, or 44.5° C. or more, or 45° C. or more. In some embodiments where the subject is a human, the volatile liquid can have a vaporization temperature ranging from 37° C. to 45° C., such as 37.5° C. to 45° C., or 37.5° C. to 43° C., or 37.5° C. to 40° C. In other instances, the volatile liquid may have a vaporization temperature substantially the same as the typical body temperature of the subject, or slightly lower than the typical body temperature of the subject. For example, if the subject is a human and the typical body temperature is 37° C., in these cases the volatile liquid can have a vaporization temperature of 37° C., or in some cases 37° C. or less, or 36.5° C. or less, or 36° C. or less, or 35.5° C. or less, or 35° C. or less, such as for example a vaporization temperature ranging from 35° C. to 37° C.

In order to provide sufficient heat above the normal body temperature of the subject to vaporize the volatile liquid, a heat generating material can be included in the active agent delivery device. For example, the device can include an additional reservoir (e.g., a heat reservoir) that contains a heat generating material. The heat reservoir can be positioned in the device in a heat transfer relationship with the power reservoir that contains the gas generating volatile liquid. By "heat transfer relationship" is meant that the heat reservoir is positioned in the device such that heat produced by the heat generating material in the heat reservoir can be transferred (e.g., by thermal conduction) to the power reservoir. The heat provided to the power reservoir from the heat generating material can be sufficient to heat the volatile liquid in the power reservoir to its vaporization temperature, such that the volatile liquid vaporizes and produces a gas in the power reservoir, thus increasing the pressure in the power reservoir as described herein. Heat generating materials that can be used in the active agent delivery devices include heat generating materials that produce heat upon contact with an aqueous medium (e.g., water or an aqueous medium contained in a subject, such as an aqueous medium in an intestine, stomach, mouth, vagina, anus, urethra, etc. of a subject). Examples of heat generating materials include, but are not limited to, calcium chloride, and the like.

Pressures generated by the active agent delivery device are sufficient to deliver the active agent formulation into and/or through the mucosal layer in the subject and can be 25 kPa or more, such as 30 kPa or more, or 35 kPa or more, or 40 kPa or more, or 45 kPa or more, or 50 kPa or more, or 55 kPa or more, or 60 kPa or more, or 65 kPa or more, or 70 kPa or more, or 75 kPa or more, or 80 kPa or more, or 85 kPa or more, or 90 kPa or more, or 95 kPa or more, or 100 kPa or more, or 105 kPa or more, or 110 kPa or more, or 115 kPa or more, or 120 kPa or more, or 125 kPa or more, or 130 kPa or more, or 135 kPa or more, or 140 kPa or more, or 145 kPa or more, or 150 kPa or more. In some cases, the pressure generated by the active agent delivery device (e.g., produced inside the power reservoir and/or active agent reservoir) is 30 kPa. For example, the pressure generated by the active agent delivery device can range from 25 kPa to 150 kPa, or 25 kPa to 125 kPa, or 25 kPa to 100 kPa, or 25 kPa to 75 kPa, or 25 kPa to 50 kPa, or 30 kPa to 50 kPa. In some cases, the pressure generated by the active agent delivery device ranges from 30 kPa to 50 kPa. In some instances, the pressure generated by the active agent delivery device as described above is measured as the difference in pressure between the surrounding environment and the pressure at an active agent delivery nozzle of the device.

In certain embodiments, the active agent delivery device is configured to release the active agent formulation contained in an active agent reservoir of the device in a short time period, such as in 10 milliseconds (msec) or less, such as 9 msec or less, or 8 msec or less, or 7 msec or less, or 6 msec or less, or 5 msec or less, or 4 msec or less, or 3 msec or less, or 2 msec or less, or 1 msec or less, or 0.5 msec or less, or 0.3 msec or less, or 0.1 msec or less. For example, the active agent delivery device can release the active agent formulation contained in an active agent reservoir of the device in a short time period ranging from 0.1 msec to 10 msec, or 0.1 msec to 9 msec, or 0.1 msec to 8 msec, or 0.1 msec to 7 msec, or 0.1 msec to 6 msec, or 0.1 msec to 5 msec, or 0.1 msec to 4 msec, or 0.1 msec to 3 msec, or 0.1 msec to 2 msec, or 0.1 msec to 1 msec, or 0.1 msec to 0.5 msec. In some cases, the active agent delivery device releases the active agent formulation contained in an active agent reservoir of the device in 5 msec or less. In some cases, the active agent delivery device releases the active agent formulation contained in an active agent reservoir of the device in 4 msec or less. In some cases, the active agent delivery device releases the active agent formulation contained in an active agent reservoir of the device in 3 msec or less. In some cases, the active agent delivery device releases the active agent formulation contained in an active agent reservoir of the device in 2 msec or less. In some cases, the active agent delivery device releases the active agent formulation contained in an active agent reservoir of the device in 1 msec or less.

In some embodiments, the active agent delivery device is configured to release the active agent formulation contained in an active agent reservoir of the device at a high velocity sufficient to deliver the active agent formulation into and/or through the mucosal layer in the subject. For example, the velocity of the active agent formulation can be 0.1 meter/second (m/s) or more, such as 0.5 m/s or more, or 1 m/s or more, or 1.5 m/s or more, or 2 m/s or more, or 2.5 m/s or more, or 3 m/s or more, or 3.5 m/s or more, or 4 m/s or more, or 4.5 m/s or more, or 5 m/s or more, or 5.5 m/s or more, or 6 m/s or more, or 6.5 m/s or more, or 7 m/s or more, or 7.5 m/s or more, or 8 m/s or more, or 8.5 m/s or more, or 9 m/s or more, or 9.5 m/s or more, or 10 m/s or more. In some cases, the velocity of the active agent formulation can range from 0.1 m/s to 10 m/s, such as 0.5 m/s to 9 m/s, or 1 m/s to 8 m/s, or 2 m/s to 7 m/s, or 2 m/s to 6 m/s, or 2 m/s to 5 m/s, or 3 m/s to 5 m/s. For example, in some embodiments, the velocity of the active agent formulation released from the device is 4 m/s. In some embodiments, the velocity of the active agent formulation released from the device is 2.5 m/s.

As described above, the aqueous medium that can be used to activate the gas generating material and/or the heat generating material in the active agent delivery device can be water or an aqueous medium in the subject, such as an aqueous medium in an intestine, stomach, mouth, vagina, anus, urethra, etc. of the subject. In some instances, the aqueous medium used to activate the gas generating material and/or the heat generating material is provided by the surrounding environment within the subject after the active agent delivery device is administered to the subject, such as for example an aqueous medium in an intestine, stomach, mouth, vagina, anus, urethra, etc. of the subject.

In other embodiments, the aqueous medium (e.g., water) can be contained in an additional reservoir of the device (e.g., an aqueous medium reservoir). For example, the device can include the aqueous medium reservoir. The aqueous medium reservoir can be positioned in the device adjacent to the power reservoir. In some instances, a separator is positioned between the power reservoir and the aqueous medium reservoir. The separator can be substantially impermeable to the aqueous medium, such that the aqueous medium does not prematurely contact the contents of the power reservoir. In some cases, the separator between the power reservoir and the aqueous medium reservoir is frangible, and the device also includes a puncturing element configured to puncture and/or break the separator between the power reservoir and the aqueous medium reservoir. In these embodiments, when activation of the device is desired, the puncturing element can be contacted to the separator (e.g., by pressing the puncturing element against the separator) with sufficient force to puncture and/or break the separator, thus allowing the aqueous medium in the aqueous medium reservoir to contact the contents of the power reservoir. As described above, the power reservoir may contain a gas generating material that produces a gas upon contact with the aqueous medium.

In other embodiments, the aqueous medium reservoir can be provided as a separate element from the active agent delivery device. The aqueous medium reservoir can contain an aqueous medium. In some instances, the aqueous medium reservoir can include a frangible wall. In these embodiments, the power reservoir may have an exterior surface composed of a material configured to dissolve or degrade upon contact with an aqueous medium. The aqueous medium reservoir may be configured to contact at least a portion of the power reservoir end of the device and activate the power reservoir. For example, the aqueous medium reservoir may be configured to contact the exterior surface of the power reservoir with the aqueous medium contained in the aqueous medium reservoir. In some cases, the aqueous medium reservoir can be attached to the active agent delivery device around the power reservoir end of the device, such that the frangible wall is broken and the aqueous medium is released from the aqueous medium reservoir. Contacting the exterior surface of the power reservoir with the aqueous medium can facilitate the dissolution and/or degradation of the dissolvable/degradable surface of the power reservoir, and thus allow the aqueous medium to contact the contents of the power reservoir. As described above, the power reservoir may contain a gas generating material that produces a gas upon contact with the aqueous medium.

In certain embodiments, the device includes one or more nozzles on the active agent reservoir that separate the active agent reservoir from the exterior of the device. The nozzles provide an outlet from the active agent reservoir through which the active agent formulation can be delivered to the mucosal layer in the subject. In some cases, a nozzle is formed by providing a hole through a wall of the active agent reservoir. For example, a nozzle hole may be provided on a surface of the active agent reservoir opposite from the side of the active agent reservoir that is adjacent to the movable separator in the device. In some cases, nozzles may be provided on a side wall of the device (e.g., on a side wall of the active agent reservoir). In certain embodiments, the nozzle may protrude from the exterior surface of the active agent reservoir. For example, the nozzle may be provided on a surface of the active agent reservoir opposite from the side of the active agent reservoir that is adjacent to the movable separator in the device. The nozzle can be cone shaped, cylinder shaped, pyramid shaped, frustum shaped, or may have a cross-sectional profile of a square, or a rectangle, etc. In some instances, a nozzle that protrudes from a surface of the active agent reservoir may have a longitudinal axis substantially perpendicular to the surface of the active agent reservoir. In other embodiments, the nozzle may be angled with respect to the surface of the active agent reservoir. In yet other embodiments, the nozzle can extend from a side wall of the device (e.g., extend from a side wall of the active agent reservoir). In some cases, a nozzle that extends from a side wall of the device may facilitate delivery of the active agent to a mucosal layer positioned alongside of the device, such as in a nasal cavity.

In certain embodiments, the nozzle can include a valve. The valve (i.e., the active agent reservoir valve) can be configured to release the active agent formulation from the active agent reservoir upon a certain condition. For instance, the active agent reservoir valve may be configured to release the active agent formulation from the active agent reservoir when a threshold pressure is achieved in the active agent reservoir due to the application of pressure on the active agent reservoir from the power reservoir. In other instances, the active agent reservoir valve may be configured to release the active agent formulation from the active agent reservoir in response to a change in a condition of the surrounding environment, such as, but not limited to, pH, temperature, exposure to an aqueous medium, and the like. For example, the active agent reservoir valve may be composed of a material that is a pH responsive material, such as a pH responsive material that dissolves or degrades at a relatively low pH (e.g., pH 5 or less, or pH 4 or less, or pH 3 or less, or pH 2 or less). An active agent reservoir valve composed of a pH responsive material that dissolves or degrades at low pH may facilitate release of the active agent in the stomach of the subject. In other embodiments, the valve may be composed of a material that is a pH responsive material, such as a pH responsive material that dissolves or degrades at a relatively higher pH (e.g., pH 5 or more, or pH 6 or more, or pH 7 or more). An active agent reservoir valve composed of a pH responsive material that dissolves or degrades at a relatively higher pH may facilitate release of the active agent in the intestine of the subject.

One or more valves may also be present on the power reservoir (i.e., power reservoir valves). The power reservoir valve can be configured to provide an inlet into the power reservoir upon a certain condition. For example, the valve on the power reservoir can provide an inlet through which an aqueous medium can contact the contents of the power reservoir, e.g., to activate a pressure generating material in the power reservoir. In some instances, the power reservoir valve may be configured to provide an inlet into the power reservoir in response to a change in a condition of the surrounding environment, such as, but not limited to, pH, temperature, exposure to an aqueous medium, and the like. For example, the power reservoir valve may be composed of a material that is a pH responsive material, such as a pH responsive material that dissolves or degrades at a relatively low pH (e.g., pH 5 or less, or pH 4 or less, or pH 3 or less, or pH 2 or less). A power reservoir valve composed of a pH responsive material that dissolves or degrades at low pH may facilitate activation of the pressure generating material in the power reservoir in the stomach of the subject. In other embodiments, the power reservoir valve may be composed of a material that is a pH responsive material, such as a pH responsive material that dissolves or degrades at a relatively higher pH (e.g., pH 5 or more, or pH 6 or more, or pH 7 or more). A power reservoir valve composed of a pH responsive material that dissolves or degrades at a relatively higher pH may facilitate activation of the pressure generating material in the power reservoir in the intestine of the subject.

In certain embodiments (e.g., embodiments of the active agent delivery device that include a heat reservoir), one or more valves may also be present on the heat reservoir (i.e., power reservoir valves). The heat reservoir valve can be configured to provide an inlet into the heat reservoir upon a certain condition. For example, the valve on the heat reservoir can provide an inlet through which an aqueous medium can contact the contents of the heat reservoir, e.g., to activate a heat generating material in the heat reservoir. In some instances, the heat reservoir valve may be configured to provide an inlet into the heat reservoir in response to a change in a condition of the surrounding environment, such as, but not limited to, pH, temperature, exposure to an aqueous medium, and the like. For example, the heat reservoir valve may be composed of a material that is a pH responsive material, such as a pH responsive material that dissolves or degrades at a relatively low pH (e.g., pH 5 or less, or pH 4 or less, or pH 3 or less, or pH 2 or less). A heat reservoir valve composed of a pH responsive material that dissolves or degrades at low pH may facilitate activation of the heat generating material in the heat reservoir in the stomach of the subject. In other embodiments, the heat reservoir valve may be composed of a material that is a pH responsive material, such as a pH responsive material that dissolves or degrades at a relatively higher pH (e.g., pH 5 or more, or pH 6 or more, or pH 7 or more). A heat reservoir valve composed of a pH responsive material that dissolves or degrades at a relatively higher pH may facilitate activation of the heat generating material in the heat reservoir in the intestine of the subject.

The one or more valves included in the active agent delivery device (e.g., active agent reservoir valve, power reservoir valve, heat reservoir valve, etc.) can be composed of any suitable material, such as, but not limited to a pH responsive material (e.g., a pH responsive material that dissolves or degrades at relatively low or relatively high pH), a temperature responsive material (e.g., a temperature responsive material that dissolves or degrades at or above the normal body temperature of the subject, such as at 37° C.), a material that dissolves or degrades upon exposure to an aqueous medium, and the like. Examples of suitable valve materials include, but are not limited to, pH responsive polymers, temperature responsive polymers, or polymers that dissolve or degrade in an aqueous medium, and the like.

The active agent delivery device may have a variety of different cross-sectional configurations, where the cross-sectional configuration is the shape defined by the walls of the enclosure containing the active agent reservoir and the power reservoir. Cross-sectional configurations of interest include, but are not limited to circular, rectangular, triangular, square and oval, combinations thereof, as well as irregular cross sectional configurations. In some instances, the device is composed of a tubular member (e.g., a cylinder) that has a planar surface at the active agent reservoir end of the device and a hemispherical structure at the power reservoir end of the device. In other embodiments, the active agent delivery device may be configured as a low-profile active agent delivery device. By "low-profile" is meant that the thickness of the device is less than the length or width of the device. Such low-profile devices may facilitate delivery of the active agent formulation to a mucosal layer in the subject, such as for buccal delivery of an active agent. For example, a low-profile device may have a length or width to thickness ratio of 2:1 or more, such as 3:1 or more, or 4:1 or more, or 5:1 or more, or 6:1 or more, or 7:1 or more, or 8:1 or more, or 9:1 or more, or 10:1 or more.

Devices described herein may have varied dimensions, as desired. In some instances, the length of the device ranges from 1 mm to 50 mm, such as 5 mm to 30 mm, and including 10 mm to 20 mm. The outer diameter of the device may vary, ranging in some instances from 1 mm to 30 mm, such as 5 mm to 20 mm and including 5 mm to 10 mm. The inner diameter of the device may also vary, ranging from 0.5 mm to 29.99 mm, such as 3.0 mm to 19.99 mm and including 3.0 mm to 9.99 mm. The walls of the device may vary in thickness, so long as the walls are sufficiently thick to hold the active agent formulation in the active agent reservoir, sufficiently thick to hold the pressure generating material in the power reservoir and/or sufficiently thick to hold the heat generating material in the heat reservoir, and so long as the walls are sufficiently thick to provide for the desired pressure within the power reservoir and/or the active agent reservoir without unintended rupture of the device. In some instances, the walls range in thickness from 0.01 mm to 2 mm, such as 0.01 mm to 0.2 mm and including 0.01 mm to 0.1 mm. The dimensions may be constant or variable in the device, as desired. For example, the inner diameter may be constant along the length of the device, or may vary.

Device components may be fabricated from any convenient material using any convenient protocol. Materials of interest from which the device components may be fabricated include physiologically acceptable polymeric materials that are used in conventional pharmaceutical dosage forms and/or medical devices or implants. The materials may be clear or opaque, and may be colored as desired. Of interest are both rigid and elastic materials. For example, a device having rigid walls may facilitate generating a sufficient pressure to deliver an active agent formulation into and/or through mucosal membranes in a subject. The devices may be fabricated using and convenient fabrication protocol, including but not limited to, 3D printing, molding, and the like.

Suitable polymers from which device components (e.g., the enclosure of the device, the power reservoir, the active agent reservoir, the heat reservoir, the nozzle, the valves, etc.) may be fabricated include, but are not limited to: gelatins, polyvinyl alcohol (PVA); natural and synthetic polysaccharides, including pullulan, carrageenan, xanthan, chitosan agar gums, and cellulosic materials, such as carboxymethylcellulose, hydroxypropylmethylcellulose (HPMC), methylcellulose, hydroxyethylcellulose, hydroxyethyl methylcellulose, hydroxypropylcellulose; polyethylene glycols (PEGs), polyethylene oxides (PEOs), mixtures of PEGs and PEOs; acrylic and methacrylic acid based polymers, such as EUDRAGIT E™, EUDRAGIT L™ and/or EUDRAGIT S™ methacrylic acid polymers), EUDRAGIT RL™ and/or EUDRAGIT RS™ ammonium methacrylate copolymers; povidone (polyvinyl pyrrolidone), polyglycolysed glycerides (such as GELUCIRE 44/14™, GELUCIRE 50/02™, GELUCIRE 50/13™ and GELUCIRE 53/10™ polymers); carboxyvinyl polymers (such as CARBOPOL™ polymers); polyoxyethylene-polyoxypropylene copolymers (such as POLOXAMER 188™ polymer); and the like.

The device components may be fabricated using any convenient protocol, including molding, 3D printing, etc. Fabrication protocols of interest include, but are not limited to, those described in U.S. Pat. Nos. 5,705,189; 4,576,284; 4,591,475; 4,655,840; 4,738,724; 4,738,817 and 4,790,881; the disclosures of which are herein incorporated by reference.

A variety of active agents may be delivered by the active agent delivery devices described herein. In embodiments of the device, the active agent formulation includes an active agent component (made of a single type of active agent or two or more different types of active agents). The term "active agent" refers to any compound or mixture of compounds which produces a desired physiological result in the subject, e.g., a beneficial or useful result, such as a therapeutic result, upon contact with a living organism, e.g., an animal, such as a human. Active agents are distinguishable from other components of the active agent formulation, such as carriers, diluents, lubricants, binders, colorants, etc. The active agent may be any molecule, as well as a binding portion or fragment thereof, that is capable of modulating a biological process in a living subject. In certain embodiments, the active agent may be a substance used in the diagnosis, treatment, or prevention of a disease or as a component of a medication.

The active agent is a compound that interacts with a target in a living subject. The target may be a number of different types of naturally occurring structures, where targets of interest include both intracellular and extra-cellular targets.

Such targets may be proteins, phospholipids, nucleic acids, and the like. The active agent may include one or more functional groups that provide for structural interaction with the target, e.g., groups that provide for hydrophobic, hydrophilic, electrostatic or covalent interactions, depending on the particular active agent and its intended target, where functional groups of interest include groups that participate in hydrogen bonding, hydrophobic-hydrophobic interactions, electrostatic interactions, etc., and may include at least an amine, amide, sulfhydryl, carbonyl, hydroxyl or carboxyl group, such as at least two functional chemical groups. Active agents of interest may include cyclical carbon or heterocyclic structures and/or aromatic or polyaromatic structures substituted with one or more of the above functional groups. Also of interest as moieties of active agents are structures found among biomolecules, including proteins, peptides, vaccines, adjuvants, saccharides, fatty acids, steroids, purines, pyrimidines, derivatives, structural analogs, or combinations thereof. Such compounds may be screened to identify those of interest using any convenient screening protocol.

The active agents may be derived from a naturally-occurring or synthetic compound that may be obtained from a wide variety of sources, including food, pollens and libraries of synthetic or natural compounds. For example, numerous protocols are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the active agent may be obtained from a library of naturally-occurring or synthetic molecules, including a library of compounds produced through combinatorial means, i.e., a compound diversity combinatorial library. When obtained from such libraries, the active agent employed will have demonstrated some desirable activity in an appropriate screening assay for the activity. Combinatorial libraries, as well as methods for producing and screening such libraries, are known in the art and described in: U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Active agents of interest include both small molecule and large molecule active agents, including macromolecule active agents. Small molecule active agents include those that are 5,000 daltons (Da) or less, such as 2,500 daltons or less, or 1,000 daltons or less. Large molecule active agents include those that are 5,000 daltons or more, or 7,500 daltons or more, such as 10,000 daltons or more, including 50,000 daltons or more, such as 100,000 daltons or more. In some instances, the active agent is a macromolecule, e.g., a very large molecule, such as a colloidal particle, protein, or a polymer, that may be composed of hundreds or thousands of atoms.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; vaccines; therapeutic proteins; antigens, epitopes and hormones etc. Active agents of interest include, but are not limited to: antibiotics, such as: aminoglycosides, e.g. amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g. azidamfenicol, chloramphenicol, florfenicol, and theimaphenicol; ansamycins, e.g. rifamide, rifampin, rifamycin, rifapentine, rifaximin; b-lactams, e.g. carbacephems, carbapenems, cephalosporins, cehpamycins, monobactams, oxaphems, penicillins; lincosamides, e.g. clinamycin, lincomycin; macrolides, e.g. clarithromycin, dirthromycin, erythromycin, etc.; polypeptides, e.g. amphomycin, bacitracin, capreomycin, etc.; tetracyclines, e.g. apicycline, chlortetracycline, clomocycline, minocycline, etc.; synthetic antibacterial agents, such as 2,4-diaminopyrimidines, nitrofurans, quinolones and analogs thereof, sulfonamides, sulfones; antifungal agents, such as: polyenes, e.g. amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g. butenafine, naftifine, terbinafine; imidazoles, e.g. bifonazole, butoconazole, chlordantoin, chlormidazole, etc., thiocarbamates, e.g. tolciclate, triazoles, e.g. fluconazole, itraconazole, terconazole; anthelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.; antimalarials, such as: acedapsone, amodiaquin, arteether, artemether, artemisinin, artesunate, atovaquone, bebeerine, berberine, chirata, chlorguanide, chloroquine, chlorprogaunil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate; antiprotozoan agents, such as: acranil, tinidazole, ipronidazole, ethylstibamine, pentamidine, acetarsone, aminitrozole, anisomycin, nifuratel, tinidazole, benzidazole, suramin; cardioprotective agents, e.g., Zinecard (dexrazoxane); blood modifiers, including anticoagulants (e.g., coumadin (warfarin sodium), fragmin (dalteparin sodium), heparin, innohep (tinzaparin sodium), lovenox (enoxaparin sodium), orgaran (danaparoid sodium)) anti-platelet agents (e.g., aggrasta (tirofiban hydrochloride), aggrenox (aspirin/extended release dipyridamole), agrylin (anagrelide hydrochloride), ecotrin (acetylsalicylic acid), folan (epoprostenol sodium), halfprin (enteric coated aspirin), integrlilin (eptifibatide), persantine (dipyridamole USP), plavix (clopidogrel bisulfate), pletal (cilostazol), reopro (abciximab), ticlid (ticlopidine hydrochloride)), thrombolytic agents (activase (alteplase), retavase (reteplase), streptase (streptokinase)); adrenergic blockers, such as cardura (doxazosin mesylate), dibenzyline (phenoxybenzamine hydrochloride), hytrin (terazosin hydrochloride), minipress (prazosin hydrochloride), minizide (prazosin hydrochloride/polythiazide); adrenergic stimulants, such as aldoclor (methyldopa-chlorothiazide), aldomet (methyldopa, methyldopate HCI), aldoril (methyldopa-hydrochlorothiazide), catapres (clonidine hydrochloride USP, clonidine), clorpres (clonidine hydrochloride and chlorthalidone), combipres (clonidine hydrochloride/chlorthalidone), tenex (guanfacine hydrochloride); alpha/bet adrenergic blockers, such as coreg (carvedilol), normodyne (labetalol hydrochloride); angiotensin converting enzyme (ACE) inhibitors, such as accupril (quinapril hydrochloride), aceon (perindopril erbumine), altace (ramipril), captopril, lotensin (benazepril hydrochloride), mavik (trandolapril), monopril (fosinopril sodium tablets), prinivil (lisinopril), univasc (moexipril hydrochloride), vasotec (enalaprilat, enalapril maleate), zestril (lisinopril); angiotensin converting enzyme (ACE) inhibitors with calcium channel blockers, such as lexxel (enalapril maleate-felodipine ER), lotrel (amlodipine and benazepril hydrochloride), tarka (trandolapril/verapamil hydrochloride ER); angiotensin converting enzyme (ACE) inhibitors with diuretics, such as accuretic (quinapril HCI/hydroclorothiazide), lotensin (benazepril hydrochloride and hydrochlorothiazide USP), prinizide (lisinopril-hydrochlorothiazide), uniretic (moexipril hydrochloride/hydrochlorothiazide), vaseretic (enalapril maleate-hydrochlorothiazide), zestoretic (lisinopril and hydrochlorothiazide); angiotensin II receptor antagonists, such as atacand (candesartan cilexetil), avapro (irbesartan), cozaar (losartan potassium), diovan (valsartan), micardis (telmisartan), teveten (eprosartan mesylate); angiotensin II receptor antagonists with diuretics, such as avalide (irbesartan-hydrochlorothiazide), diovan (valsartan and hydrochlorothiazide), hyzaar (losartan potassium-hydrochlorothiazide); antiarrhythmics, such as Group I (e.g., mexitil (mexiletine hydrochloride, USP), norpace (disopyramide phosphate), procanbid (procainamide hydrochloride), quinaglute (quinidine gluconate), quinidex (quinidine sulfate), quinidine (quinidine gluconate injection, USP), rythmol (propafenone hydrochloride), tambocor (flecainide acetate), tonocard (tocainide HCI)), Group II (e.g., betapace (sotalol HCI), brevibloc (esmolol hydrochloride), inderal (propranolol hydrochloride), sectral (acebutolol hydrochloride)), Group III (e.g., betapace (sotalol HCI), cordarone (amiodarone hydrochloride), corvert (ibutilide fumarate injection), pacerone (amiodarone HCI), tikosyn (dofetilide)), Group IV (e.g., calan (verapamil hydrochloride), cardizem (diltiazem HCI), as well as adenocard (adenosine), lanoxicaps (digoxin), lanoxin (digoxin)); anti-lipemic acids, including bile acid sequestrants (e.g., colestid (micronized colestipol hydrochloride), welchol (colesevelam hydrochloride)), fibric acid derivatives (e.g., atromid (clofibrate), lopid (gemfibrozal tablets, USP), tricor (fenofibrate capsules)), HMG-CoA reductase inhibitors (e.g., baycol (cerivastatin sodium tablets), lescol (fluvastatin sodium), lipitor (atorvastatin calcium), mevacor (lovastatin), pravachol (pravastatin sodium), zocor (simvastatin)), Nicotinic Acid (e.g., Niaspan (niacin extended release tablets)); beta adrenergic blocking agents, e.g., betapace (sotalol HCI), blocadren (timolol maleate), brevibloc (esmolol hydrochloride), cartrol (carteolol hydrochloride), inderal (propranolol hydrochloride), kerlone (betaxolol hydrochloride), nadolol, sectral (acebutolol hydrochloride), tenormin (atenolol), toprol (metoprolol succinate), zebeta (bisoprolol fumarate); beta adrenergic blocking agents with diuretics, e.g., corzide (nadolol and bendroflumethiazide tablets), inderide (propranolol hydrochloride and hydroclorothiazide), tenoretic (atenolol and chlorthalidone), timolide (timolol maleate-hydrochlorothiazide), ziac (bisoprolol fumarate and hydrochlorothiazide); calcium channel blockers, e.g., adalat (nifedipine), calan (verapamil hydrochloride), cardene (nicardipine hydrochloride), cardizem (diltiazem HCI), covera (verapamil hydrochloride), isoptin (verapamil hydrochloride), nimotop (nimodipine), norvasc (amlodipine besylate), plendil (felodipine), procardia (nifedipine), sular (nisoldipine), tiazac (diltiazem hydrochloride), vascor (bepridil hydrochloride), verelan (verapamil hydrochloride); diuretics, including carbonic anhydrase inhibitors (e.g., daranide (dichlorphenamide)), combination diuretics (e.g., aldactazide (spironolactone with hydrochlorothiazide), dyazide (triamterene and hydrochlorothiazide), maxzide (triamterene and hydrochlorothiazide), moduretic (amiloride HCI-hydrochlorothiazide)), loop diuretics (demadex (torsemide), edecrin (ethacrynic acid, ethacrynate sodium), furosemide), potassium-sparing diuretics (aldactone (spironolactone), dyrenium (triamterene), midamor (amiloride HCI)), thiazides & related diuretics (e.g., diucardin (hydroflumethiazide), diuril (chlorothiazide, chlorothiazide sodium), enduron (methyclothiazide), hydrodiuril hydrochlorothiazide), indapamide, microzide (hydrochlorothiazide) mykrox (metolazone tablets), renese (polythi-azide), thalitone (chlorthalidone, USP), zaroxolyn (metolazone)); inotropic agents, e.g., digitek (digoxin), dobutrex (dobutamine), lanoxicaps (digoxin), lanoxin (digoxin), primacor (milrinone lactate); activase (alteplase recombinant); adrenaline chloride (epinephrine injection, USP); demser (metyrosine), inversine (mecamylamine HCI), reopro (abciximab), retavase (reteplase), streptase (streptokinase), tnkase (tenecteplase); vasodilators, including coronary vasodilators (e.g., imdur (isosorbide mononitrate), ismo (isosorbide mononitrate), isordil (isosorbide dinitrate), nitrodur (nitroglycerin), nitrolingual (nitroglycerin lingual spray), nitrostat (nitroglycerin tablets, USP), sorbitrate (isosorbide dinitrate)), peripheral vasodilators & combinations (e.g., corlopam (fenoldopam mesylate), fiolan (epoprostenol sodium), primacor (milrinone lactate)), vasopressors, e.g., aramine (metaraminol bitartrate), epipen (EpiPen 0.3 mg brand of epinephrine auto injector, EpiPen Jr. 0.15 mg brand of epinephrine auto injector), proamatine (midodrine hydrochloride); etc.; psychopharmacological agents, such as (1) central nervous system depressants, e.g. general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g. analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g. central antitussives (opium alkaloids and their derivatives); pharmacodynamic agents, such as (1) peripheral nervous system drugs, e.g. local anesthetics (ester derivatives, amide derivatives), (2) drugs acting at synaptic or neuroeffector junctional sites, e.g. cholinergic agents, cholinergic blocking agents, neuromuscular blocking agents, adrenergic agents, antiadrenergic agents, (3) smooth muscle active drugs, e.g. spasmolytics (anticholinergics, musculotropic spasmolytics), vasodilators, smooth muscle stimulants, (4) histamines and antihistamines, e.g. histamine and derivative thereof (betazole), antihistamines (H1-antagonists, H2-antagonists), histamine metabolism drugs, (5) cardiovascular drugs, e.g. cardiotonics (plant extracts, butenolides, pentadienolids, alkaloids from erythrophleum species, ionophores, -adrenoceptor stimulants, etc), antiarrhythmic drugs, antihypertensive agents, antilipidemic agents (clofibric acid derivatives, nicotinic acid derivatives, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g. digestants (stomachics, choleretics), antiulcer drugs, antidiarrheal agents, (8) locally acting drugs; chemotherapeutic agents, such as (1) anti-infective agents, e.g. ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e. antineoplastic agents or cytotoxic drugs, such as alkylating agents, e.g. Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CccNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g. Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and he like; antibiotics, e.g. Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g. Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like.

Drug compounds of interest are also listed in: Goodman & Gilman's, The Pharmacological Basis of Therapeutics (9th Ed) (Goodman et al. eds) (McGraw-Hill) (1996); and 2001 Physician's Desk Reference.

Specific categories and examples of active agents include, but are not limited to those appearing the following table:

| Therapeutic Category | Pharmacological Class | Structural Examples |
|---|---|---|
| Analgesics | Opioid Analgesics | Includes drugs such as Morphine, Meperidine and Propoxyphene |
| | Non-opioid Analgesics | Includes drugs such as Sodium Salicylate, Diflunisal, Para-Aminophenol Derivatives, Anthranilic Acid Derivatives, and Phenylpropionic Acid Derivatives |
| Anesthetics | | |
| Antibacterials | Beta-lactam, Cephalosporins | |
| | Beta-lactam, Penicillins | |
| | Beta-lactam, Other | Includes drugs such as Loracarbef |
| | Macrolides | |
| | Quinolones | |
| | Sulfonamides | |
| | Tetracyclines | |
| | Antibacterials, Other | Includes drugs such as Trimethoprim, Vancomycin, Lincomycin, Clindamycin, Furazolidone, Nitrofurantoin, Linezolid, Bacitracin, Chloramphenicol, Daptomycin, Fosfomycin, Methenamine, Metronidazole, Mupirocin, Rifaximin, Spectinomycin |
| Anticonvulsants | Calcium Channel Modifying Agents | Includes drugs such as Nifedipine |
| | Gamma-aminobutyric Acid (GABA) Augmenting Agents | Includes drugs such as Clonazepam, Diazepam, and Phenobarbital |
| | Glutamate Reducing Agents | |
| | Sodium Channel Inhibitors | |
| Antidementia Agents | Cholinesterase Inhibitors | |
| | Glutamate Pathway Modifiers | |
| | Antidementia Agents, Other | Includes drugs such as Ergoloid Mesylates |
| Antidepressants | Monoamino Oxidase (Type A) Inhibitors | |
| | Reuptake Inhibitors | |
| | Antidepressants, Other | Includes drugs such as Bupropion, Maprotiline, Mirtazapine, Trazodone |
| Antiemetics | | |
| Antifungals | | Includes drugs such as Amphotericin B, and Ketoconazole |
| Antigout Agents | | |
| Anti-inflammatories | Glucocorticoids | See Adrenal Pharmacologic Class for similar/related therapies |
| | Nonsteroidal Anti-inflammatory Drugs (NSAIDs) | See Non-opioid Analgesics Pharmacologic Class for similar/related therapies |
| Antimigraine Agents | Abortive | See Analgesics Therapeutic Category for similar/related therapies |

-continued

| Therapeutic Category | Pharmacological Class | Structural Examples |
|---|---|---|
| | Prophylactic | See Autonomic Agents and Cardiovascular Agents Therapeutic Categories for similar/related therapies |
| Antimycobacterials | Antituberculars | Includes drugs such as Isoniazid, Pyridoxine and Cycloserine |
| | Antimycobacterials, Other | Includes drugs such as Clofazimine, Dapsone, Rifabutin |
| Antineoplastics | Alkylating Agents | Includes drugs such as Chlorambucil, Thiotepa, Busulfan, Dacarbazine, and Carmustine |
| | Antimetabolites | Includes drugs such as Methotrexate, Cytarabine, and Mercaptopurine |
| | Immune Modulators and Vaccines | Includes biotech drugs as various Monoclonal Antibodies, Cytokines, Interferones and Interleukins |
| | Molecular Target Inhibitors | Includes drugs such as Vaccines, Antisense and Gene Tharapies |
| | Nucleoside Analogues | Includes drugs such as dIdC, and AZT |
| | Protective Agents | Includes biotech drugs as Vaccines |
| | Topoisomerase Inhibitors | |
| | Antineoplastics, Other | Includes drugs such as Carboplatin, Cisplatin, Oxaliplatin |
| Antiparasitics | Anthelmintics | Includes drugs such as Mebendazole, Pyrantel Pamoate, Bithionol, and Paromomycin |
| | Antiprotozoals | Includes drugs such as Chloroquine, Pyrimethamine, Metronidazole, Furazolidone, Melarsoprol, Suramin and Tetracyclines |
| | Pediculicides/Scabicides | Includes drugs such as Crotamiton, Lindane, Benzyl Benzoate and Sulfur |
| Antiparkinson Agents | Catechol O-methyltransferase (COMT) Inhibitors | |
| | Dopamine Agonists | Includes drugs such as Levodopa, and Deprenyl |
| | Antiparkinson Agents, Other | Includes drugs such as Benztropine, Biperidin, Bromocriptine, Diphenhydramine, Procyclidine, Selegiline, Trihexyphenidyl |
| Antipsychotics | Non-phenothiazines | Includes drugs such as Chlorprothixene, and Thiothixene |
| | Non-phenothiazines/Atypicals | Includes drugs such as Haloperidol, Molindone, and Loxapine |
| | Phenothiazines | Includes drugs such as Fluphenazine |
| Antivirals | Anti-cytomegalovirus (CMV) Agents | Includes biotech drugs as Vaccines |
| | Antiherpetic Agents | Includes biotech drugs as Vaccines and Recombinant Proteins |
| | Anti-human immunodeficiency virus (HIV) Agents, Fusion Inhibitors | |
| | Anti-HIV Agents, Non-nucleoside Reverse Transcriptase Inhibitors | |
| | Anti-HIV Agents, Nucleoside and Nucleotide Reverse Transcriptase Inhibitors | |
| | Anti-HIV Agents, Protease Inhibitors | |
| | Anti-influenza Agents | Includes biotech drugs such as Vaccines, Flumist, and Thymidine Kinase Inhibitors |
| | Antivirals, Other | Includes drugs such as Adefovir and Ribavirin |
| Anxiolytics | Antidepressants | |
| | Anxiolytics, Other | Includes drugs such as Buspirone and Meprobamate |
| Autonomic Agents | Parasympatholytics | |
| | Parasympathomimetics | |
| | Sympatholytics | See Cardiovascular Agents and Genitourinary Agents Therapeutic Categories for similar/related therapies |
| | Sympathomimetics | See Cardiovascular Agents Therapeutic Category for similar/related therapies |
| Bipolar Agents | | |
| Blood Glucose Regulators | Antihypoglycemics | |
| | Hypoglycemics, Oral | |
| | Insulins | |
| Blood Products/Modifiers/Volume Expanders | Anticoagulants | Includes drugs such as Acetaminophen, Coumarin Derivatives, Aspirin, Heparin, and Indandione Derivatives |
| | Blood Formation Products | |
| | Coagulants | |
| | Platelet Aggregation Inhibitors | |
| Cardiovascular Agents | Alpha-adrenergic Agonists | See Autonomic Agents Therapeutic Category for similar/related therapies |
| | Alpha-adrenergic Blocking Agents | Includes drugs such as Phenolamine Mesylate, and Prazosin HCl |
| | Antiarrhythmics | Includes drugs such as Bretylium, Digitalis, Quinidine, and Atropine |
| | Beta-adrenergic Blocking Agents | Includes drugs such as Atenolol and related compounds |
| | Calcium Channel Blocking Agents | Includes drugs such as Nifedipine |
| | Direct Cardiac Inotropics | |

-continued

| Therapeutic Category | Pharmacological Class | Structural Examples |
|---|---|---|
| | Diuretics | Includes drugs such as Furosemide, and Spironolactone |
| | Dyslipidemics | |
| | Renin-angiotensin-aldosterone System Inhibitors | Includes drugs such as Captopril, and Saralasin Acetate |
| | Vasodilators | Includes drugs such as Sodium Nitroprusside, Nitroglycerine |
| Central Nervous System Agents | Amphetamines | |
| | Non-amphetamines | |
| Dental and Oral Agents | | Includes such drugs as CHG |
| Dermatological Agents | Dermatological Anesthetics | Includes drugs such as Lidocaine, Dibucaine, and Diperodon |
| | Dermatological Antibacterials | Includes drugs such as Bacitracin, Chlorotetracycline, and Erythromycin |
| | Dermatological Antifungals | Includes drugs such as Haloprogin, Tolnaftate, Imidazoles, and Polyene Antibiotics |
| | Dermatological Anti-inflammatories | Includes drugs such as Hydrocortisone, Amcinonide, and Desonide |
| | Dermatological Antipruritic Agents | Includes drugs such as Benzocaine, Lidocaine, Pramoxine, Diphenhydramine, and Hydrocortisone |
| | Dermatological Antivirals | HIV-Inhibitors of reverse transcriptase (Nucleoside analogs, Non-nucleoside analogs, and Nucleotide analogs), Viral packaging inhibitors (Protease Inhibitors), Fusion Inhibitors, Herpes Virus-Nucleoside analogs (Acyclovir, Valacyclovir, Famciclovir and Penciclovir), Interferone Alpha, and Imiquimod |
| | Dermatological Keratolytics | Includes drugs such as Urea, and Salicylic Acid |
| | Dermatological Mitotic Inhibitors | Includes drugs such as Vinblastine, and Vincristine |
| | Dermatological Photochemotherapy Agents | Includes drugs such as Hydroquinone and Trioxsalen |
| | Dermatological Retinoids | Includes drugs such as Tretinoin |
| | Dermatological Tar Derivatives | Includes drugs such as Anthraquinone derivatives (Anthralin) |
| | Dermatological Vitamin D Analogs | Includes drugs such as Calcitriol, and Calcipotriol |
| | Dermatological Wound Care Agents | Includes drugs such as Collagenase, Sutilains and Dextranomers |
| | Dermatological Antiacne | Includes drugs such as Benzoyl Peroxide, and Salicylic Acid |
| | Dermatological UVA/UVB Block | Includes actives such as 3_Benzylidene_Camphors, 2-phenylbenzimidazole-5-sulfonic acid, Octyl Salicylate, Homosalate, Octylmethyl PABA,, Octyl Methoxycinnamate, Octocrylene, Oxybenzone, Menthyl Anthranilate, Titanium Dioxide, Zinc Oxide, Avobenzone |
| Deterrents/Replacements | Alcohol Deterrents | |
| Enzyme Replacements/Modifiers | | |
| Gastrointestinal Agents | Antispasmodics, Gastrointestinal | |
| | Histamine2 (H2) Blocking Agents | Includes drugs such as Cimetidine, and Ranitidine |
| | Irritable Bowel Syndrome Agents | |
| | Protectants | |
| | Proton Pump Inhibitors | |
| | Gastrointestinal Agents, Other | Includes drugs such as Sevelamer, Ursodiol, Antisense, Vaccines and Mab and their fragments |
| Genitourinary Agents | Antispasmodics, Urinary | |
| | Benign Prostatic Hypertrophy Agents | See Autonomic Agents and Cardiovascular Agents Therapeutic Categories for similar/related therapies |
| | Impotence Agents | |
| | Prostaglandins | See Hormonal Agents, Stimulant/Replacement/Modifying TherapeuticCategory for similar/related therapies |
| Hormonal Agents, Stimulant/Replacement/ Modifying | Adrenal | See Anti-inflammatories Therapeutic Category for similar/related therapies |
| | Parathyroid/Metabolic Bone Disease Agents | |
| | Pituitary | |
| | Prostaglandins | See Genitourinary Agents Therapeutic Category for similar/related therapies |
| | Sex Hormones/Modifiers | |
| | Thyroid | Includes drugs such as Levothyroxine Sodium, and Methimazole |

-continued

| Therapeutic Category | Pharmacological Class | Structural Examples |
|---|---|---|
| Hormonal Agents, Suppressant | Adrenal | |
| | Pituitary | Includes biotech drugs as hGH |
| | Sex Hormones/Modifiers | Includes biotech drugs as Estradiol |
| | Thyroid | |
| Immunological Agents | Immune Stimulants | Includes biotech drugs as various Monoclonal Antibodies, Interferones and Interleukins |
| | Immune Suppressants | Includes biotech drugs as various Monoclonal Antibodies, Interferones and Interleukins |
| | Immunomodulators | Includes biotech drugs as various Monoclonal Antibodies, Interferones and Interleukins |
| Inflammatory Bowel Disease Agents | Glucocorticoids | See Hormonal Agents, Stimulant/Replacement/Modifying Therapeutic Category for similar/related therapies |
| | Salicylates | |
| | Sulfonamides | See Antibacterials Therapeutic Category for similar/related therapies |
| Ophthalmic Agents | Ophthalmic Anti-allergy Agents | Includes drugs such as Cromolyn |
| | Ophthalmic Antibacterials | Includes drugs such as Bacitracin, Chloramphenicol, Erythromycin, and Polymyxin B Sulfate |
| | Ophthalmic Antifungals | Includes drugs such as Amphotericin B, Miconazole, Natamycin and Nystatin |
| | Ophthalmic Antiglaucoma Agents | Includes drugs such as Pilocarpine HCl, Carbachol, Physostigmine Salicylate, Isoflurophate, and Acetazolamide |
| | Ophthalmic Anti-inflammatories | Includes drugs such as Hydrocortisone, Dexamethasone, and Medrysone |
| | Ophthalmic Antivirals | Includes drugs such as Idoxuridine, Trifluridine, Antisense, and Vidarabine |
| | Ophthalmics, Other | Includes drugs such as Formivirsen |
| Otic Agents | Otic Antibacterials | Includes drugs such as Chloramphenicol, Neomycin Sulfate, and Polymyxins |
| | Otic Anti-inflammatories | |
| Respiratory Tract Agents | Antihistamines | |
| | Antileukotrienes | |
| | Bronchodilators, Anticholinergic | |
| | Bronchodilators, Anti-inflammatories | Includes drugs such as Corticosteroid derivatives |
| | Bronchodilators, Phosphodiesterase 2 Inhibitors (Xanthines) | |
| | Bronchodilators, Sympathomimetic | Includes drugs such as Albuterol, Terbutaline, and Isoproterenol |
| | Mast Cell Stabilizers | Includes drugs such as Cromolyn Sodium |
| | Mucolytics | |
| | Respiratory Tract Agents, Other | Includes drugs such as Alpha-1-proteinase Inhibitor, Human; Benzonatate; Guaifenesin; Iodinated Glycerol; Potassium Iodide; Tetrahydrozoline |
| Sedatives/Hypnotics | | |
| Skeletal Muscle Relaxants | | Includes drugs such as Carisoprodol, Chlorphenesin Carbamate, Chlorzoxazone, and Cyclobenzaprine HCl |
| Therapeutic Nutrients/Minerals/Electrolytes | Electrolytes/Minerals | |
| | Vitamins | |
| Toxicologic Agents | Opioid Antagonists | |

In some embodiments, the active agent may be an immunogenic composition, such as, but not limited to, an antigen, an epitope, a T cell, a B cell, combinations thereof, and the like. An antigen may be a polypeptide antigen or a non-amino acid antigen. In some embodiments, the antigen can be a microbial antigen (e.g., a bacterial, viral, fungal, or parasitic antigen), a tumor antigen, or other antigens which are of interest for administration to a subject (e.g., by delivery of the antigen to the mucosal immune system as described herein) to elicit an immune response in the subject. Also of interest is modification of antigens that are useful in eliciting antibodies which can be therapeutically beneficial to the subject. In some instances, the antigen may be a tumor antigen (e.g., a fragment of a tumor from the subject) that is delivered to the mucosal immune system in the subject using the active agent delivery devices described herein in order to elicit an immune response (e.g., an increase in production of anti-tumor antibodies) that targets the tumor in the subject.

The active agent of the present disclosure can be formulated in a variety of different ways in an active agent formulation. In general, the active agent is formulated in a manner compatible with the active agent, the condition to be treated, and the route of administration to be used. The active agent can be provided in any suitable form, e.g., in the form of a pharmaceutically acceptable salt, and can be formulated to be suitable for administration into and/or through a mucosal membrane in a subject. Where the active agent is provided as a liquid formulation, the active agent can be provided as a ready-to-use dosage form that is contained in the active agent reservoir of the active agent delivery device. Methods for formulating active agents can be adapted from those available in the art. For example, an active agent can be provided in a pharmaceutical formulation that includes a therapeutically effective amount of the active agent and a pharmaceutically acceptable carrier (e.g., saline). The pharmaceutical formulation may optionally include other additives (e.g., buffers, stabilizers, preservatives, and the like). In some embodiments, the formulations are suitable for administration to a mammal, such as those that are suitable for administration to a human.

Methods

Aspects of embodiments of the present disclosure further include methods of using the devices, e.g., to deliver an active agent to a subject. Generally, methods of the present disclosure will include administering one or more active agents to a subject, for example by administering an active agent delivery device described herein to the subject. Various forms of administration are possible, depending on the target mucosal tissue. For example, the device may be administered to the subject by having the subject ingest the active agent delivery device (e.g., for delivery of an active agent to the stomach, intestine, etc.). In other embodiments, the active agent delivery device may be applied to a mucosal surface in the subject. For example, the active agent delivery device can be applied to the mucosal surface in the subject with the active agent delivery nozzle of the device facing the mucosal surface (e.g., for delivery of an active agent to a buccal or nasal mucosal surface).

Figure 4:
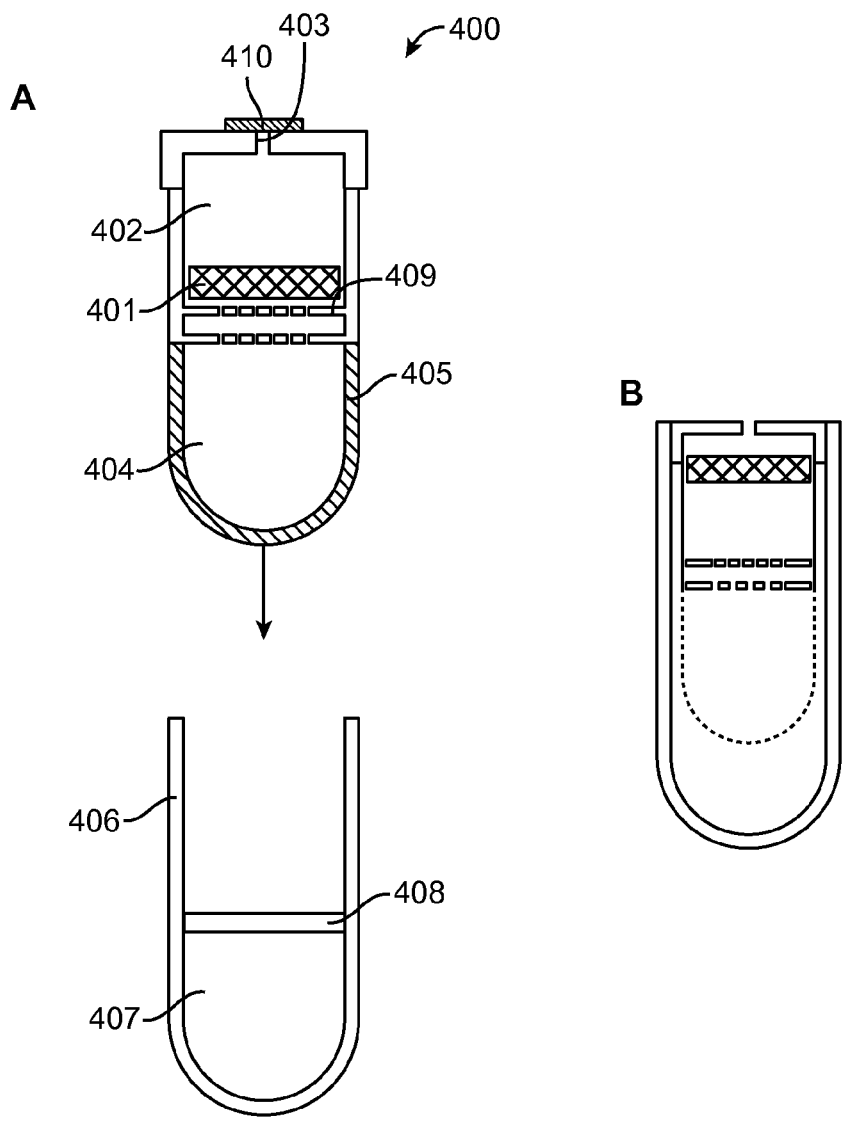
FIG. 4 provides views of an active agent delivery device where the device is activated by a gas generating chemical reaction, according to embodiments of the present disclosure.
Figure 6:
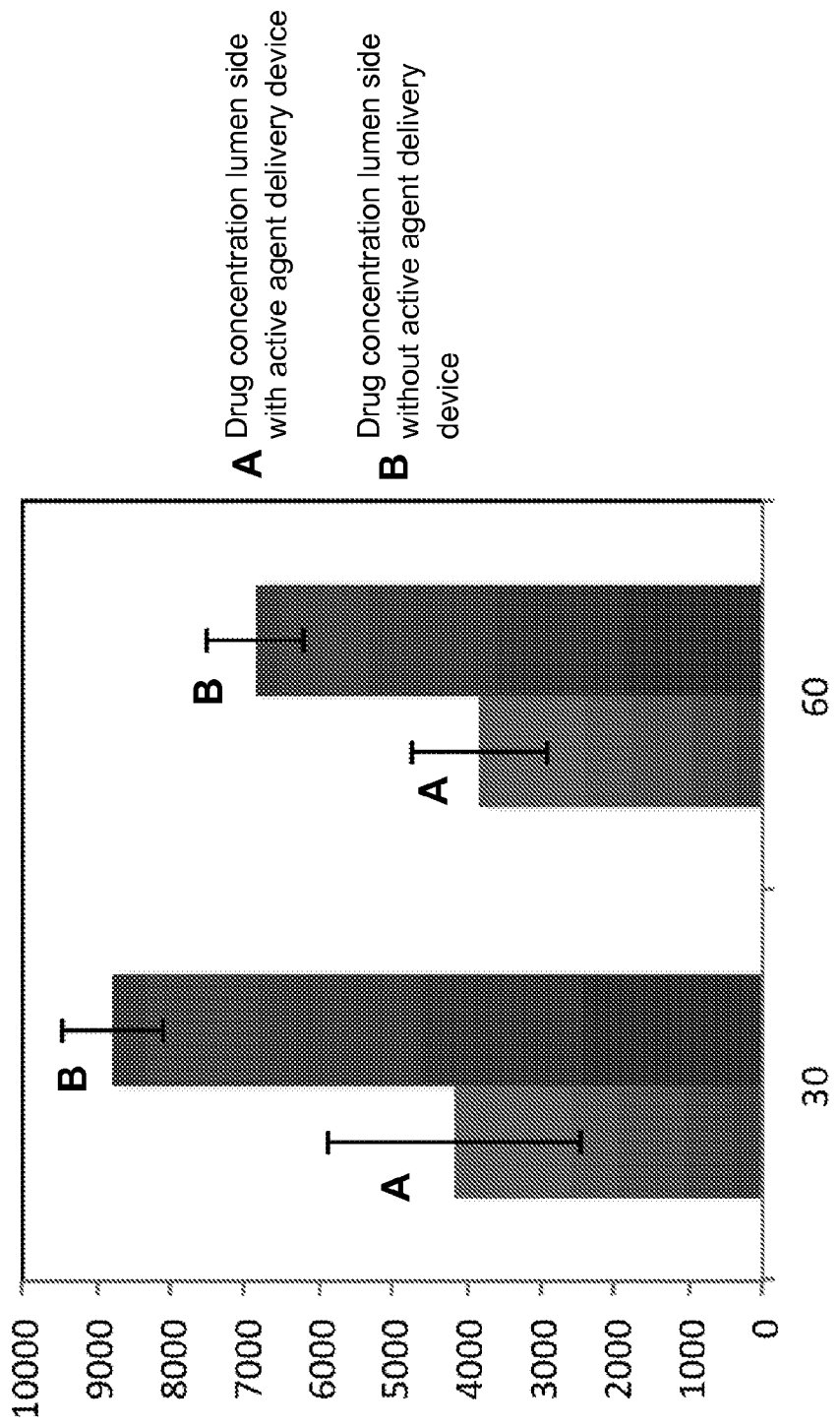
FIG. 6 provides a graph of the in vitro results from intestinal transmucosal ovalbumin delivery with and without using a device of the present disclosure in fresh pig intestinal tissue.

As described above, the active agent delivery device may be self-contained, such that the power reservoir is activated by contacting the device with the appropriate conditions within the subject, such as pH, temperature, aqueous medium, etc. In other embodiments, the active agent delivery device may be activated prior to administration to the subject. For example, as shown in FIG. 4 and described herein, an aqueous medium reservoir can be provided as a separate element from the active agent delivery device. The aqueous medium reservoir can be attached to the active agent delivery device around the power reservoir end of the device, such that a frangible wall of the aqueous medium reservoir is broken and an aqueous medium is released from the aqueous medium reservoir. As described above, contacting the exterior surface of the power reservoir with the aqueous medium can facilitate the dissolution and/or degradation of the dissolvable/degradable surface of the power reservoir, and thus allow the aqueous medium to contact the contents of the power reservoir.

Figure 11:
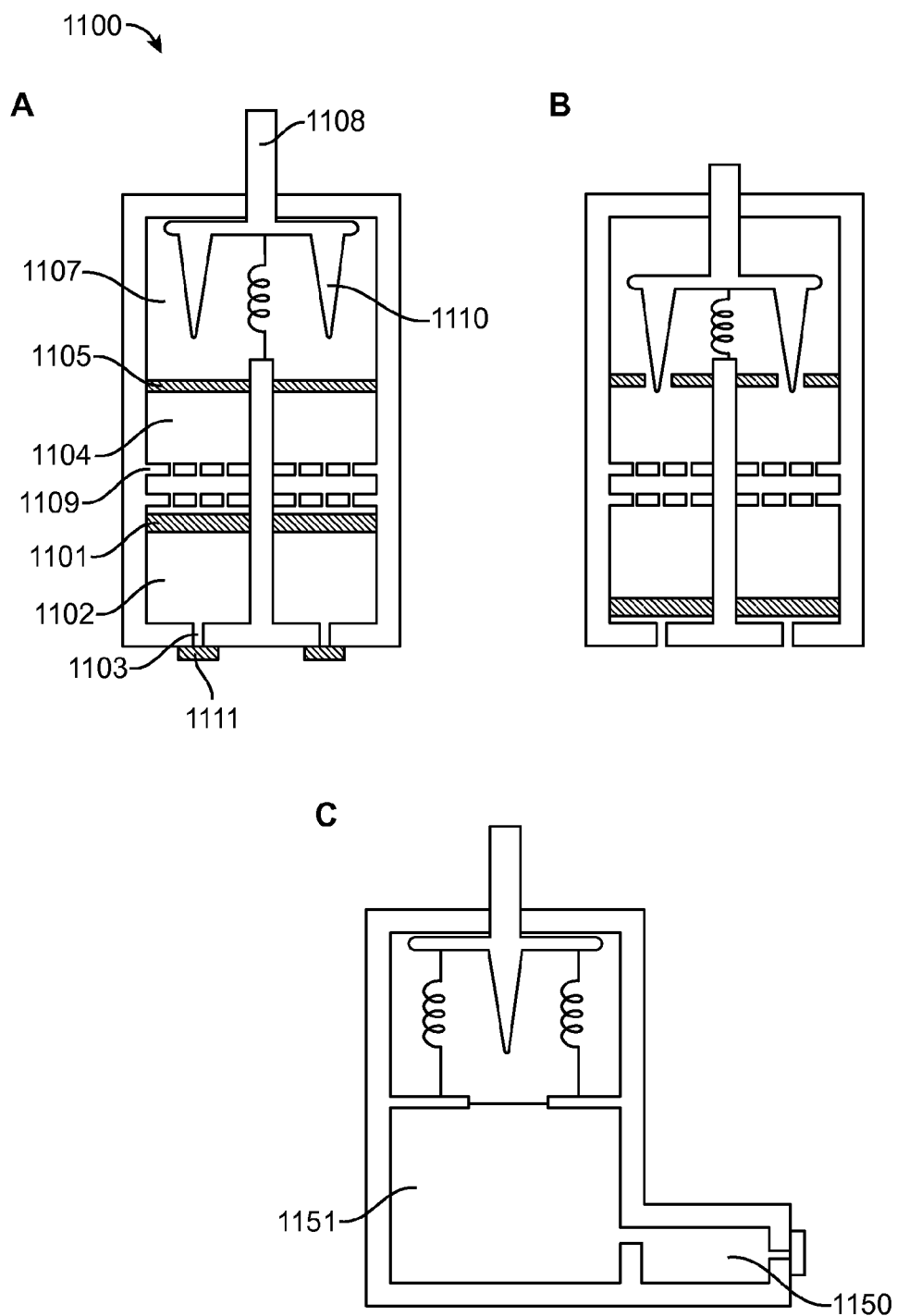
FIG. 11 provides views of an active agent delivery device where the device is activated by a gas generating chemical reaction, according to embodiments of the present disclosure.

In other embodiments, the aqueous medium can be contained in an aqueous medium reservoir in the active agent delivery device. For example, as shown in FIG. 11, the aqueous medium reservoir can be positioned in the device adjacent to the power reservoir with a frangible separator positioned between the power reservoir and the aqueous medium reservoir. In these embodiments, activation of the active agent delivery device can include puncturing and/or breaking the frangible separator between the power reservoir and the aqueous medium reservoir, such that an aqueous medium contained in the aqueous medium reservoir contacts the contents (e.g., a pressure generating material, such a gas generating material) of the power reservoir, thus activating the contents of the power reservoir.

The dosages may be administered to a variety of different types of subjects. The subject to be treated can be one that is in need of therapy, where the subject to be treated is one amenable to treatment using the active agent. Accordingly, a variety of subjects may be amenable to treatment using the active agents disclosed herein. Generally, such subjects are "mammals", with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

The active agents delivered using the active agent delivery devices disclosed herein find use in treatment of a condition or disease in a subject that is amenable to treatment by administration of the active agent. By "treatment" is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus, treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The amount of active agent administered can be initially determined based on guidance of a dose and/or dosage regimen of the parent drug. In some instances, the active agent delivery devices of the present disclosure can provide for targeted delivery, thus providing for at least one of reduced dose or reduced administrations in a dosage regimen. Thus, the active agent delivery devices can provide for reduced dose and/or reduced administration in a dosage regimen relative to the parent drug prior administered by a different means (e.g., oral dosage formulation).

In some embodiments, multiple doses of an active agent are administered. The frequency of administration of the active agent can vary depending on any of a variety of factors, e.g., severity of the symptoms, condition of the subject, etc. For example, in some embodiments, an active agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

Kits

Aspects of the present disclosure additionally include kits that include an active agent delivery device as described in detail herein. In some instances, the kit includes a packaging for containing the active agent delivery device. The packaging may be a sealed packaging, e.g., in a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). The kits may further include additional active agent delivery devices, such as two or more active agent delivery devices, which can be packed together or individually.

Also provided are containers, which may be sealed, e.g., with a resealable cap, that include one or more of the devices. The container may be sold in a kit form, e.g., with associated packaging.

In certain embodiments, the kit includes a second active agent formulation. The second active agent formulation can include, for example, a mucosal treatment agent that may be used to modify a mucosal layer in a subject. The mucosal treatment agent can, for instance, modify a physical property of the mucosal layer, such as, but not limited to, increasing permeability of the mucosal layer to active agent, increasing active agent absorption into the mucosal layer, and the like. In some cases, the mucosal treatment agent is a pre-treatment agent. By pre-treatment agent is meant that the mucosal treatment agent is administered prior to administration of the active agent delivery device to the subject. In other instances, the mucosal treatment agent may be administered substantially simultaneously with the agent delivery device. In yet other instances, the mucosal treatment agent is a post-treatment agent, where the mucosal treatment agent is administered to the subject after the agent delivery device is administered to the subject. Combinations of the above described treatment regimens may also be used.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory, etc., on which the information has been recorded or stored. Yet another form is a website address which may be used via the Internet to access the information at a removed site. Any convenient form of instructions may be present in the kits.

As can be appreciated from the disclosure provided above, embodiments of the present invention have a wide variety of applications. Accordingly, the examples presented herein are offered for illustration purposes and are not intended to be construed as a limitation on the invention in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by mass, molecular mass is mass average molecular mass, temperature is in degrees Celsius, and pressure is at or near atmospheric.

EXAMPLES

Example I

Device Activated by pH

A schematic of an active agent delivery device 100 is shown in FIG. 1, where the active agent delivery device is activated by pH. As shown in FIG. 1, panel A, the active agent delivery device 100 includes two reservoirs, the power reservoir 101 and the active agent reservoir 102, separated by a movable separator (i.e., a movable piston) 103. The power reservoir 101 contains a mixture of chemicals (citric acid and sodium bicarbonate) in a powder form. As shown in FIG. 1, panel D, the active agent delivery device 100 is administered to a subject orally. Upon arrival at the intestinal site, the active agent delivery device 100 is activated and $CO_2$ is generated inside the power reservoir 101, which increases the pressure inside the power reservoir 101. Activation of the contents of the power reservoir 101 occurs when the aqueous medium at the intestinal site enters into the power reservoir through one or more valves 105 in the power reservoir 101. Each valve 105 includes a hole the wall of the power reservoir 101, and also includes a pH sensitive material (not pictured). Upon contact of the pH sensitive material with the relatively higher pH in the intestinal site (e.g., as compared to the stomach) the pH sensitive material can degrade, thus opening the hole in the wall of the power reservoir for entry of the surrounding aqueous medium into the power reservoir 101. As shown in FIG. 1, panel B, the increase in pressure exerts a force on the piston 103, which moves the piston 103 into the active agent reservoir 102 and the active agent solution is then ejected from the nozzle 104 with high velocity.

FIG. 1, panel C, shows images of an active agent delivery device over time, where the active agent delivery device was activated and then ejected the contents of the active agent reservoir from the nozzle with high velocity.

Example II

Device Activated by Temperature and pH

Figure 2:
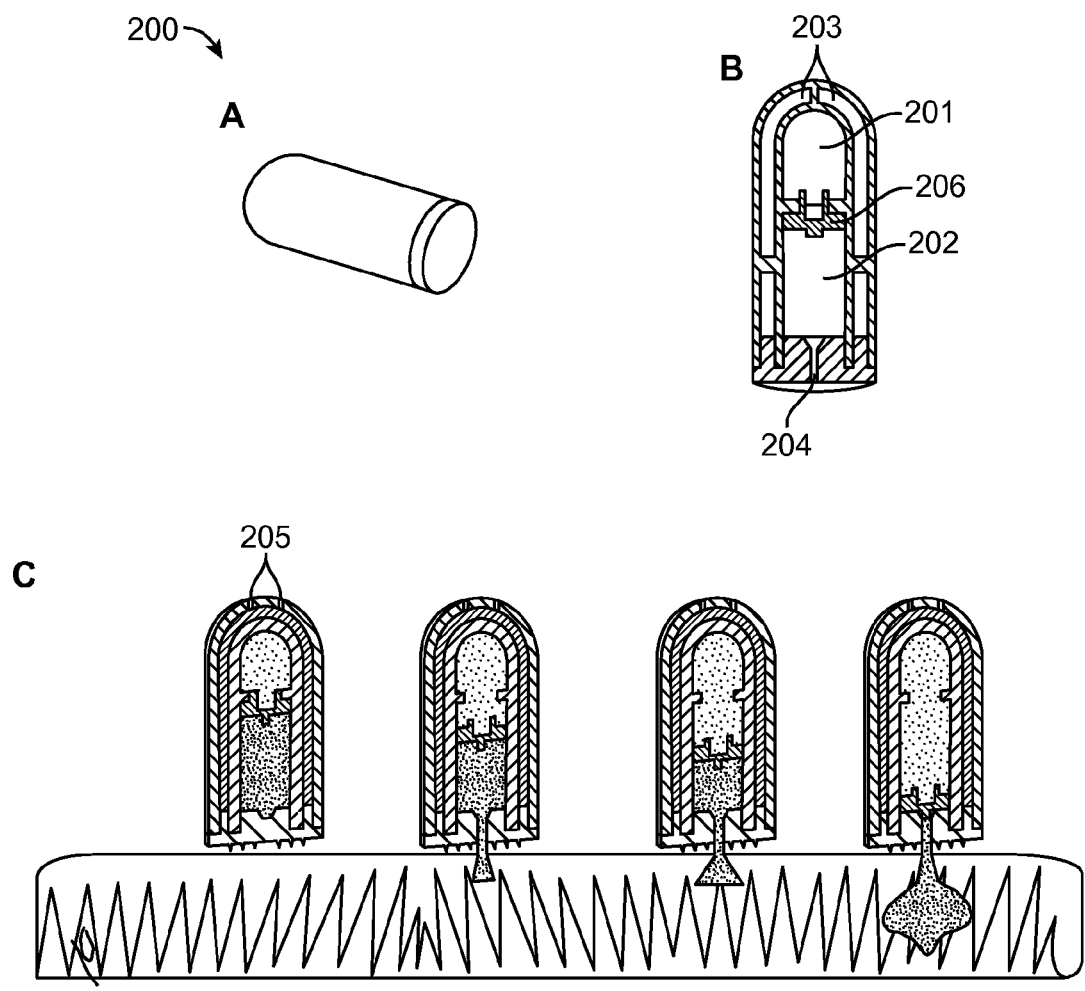
FIG. 2 provides views of an active agent delivery device where the device is activated by temperature, according to embodiments of the present disclosure.

A schematic of an active agent delivery device 200 and its ejection mechanism is shown in FIG. 2, where the active agent delivery device is activated by temperature and pH. FIG. 2, panel A, shows a side view of the device. As shown in FIG. 2, panel B, the interior of the active agent delivery device 200 includes two reservoirs separated by a movable piston 203. The power reservoir 201 contains a liquid with a vaporization temperature of 40° C. The active agent reservoir 202 contains an active agent and is sealed at one end by a freely movable guided piston 203 that separates the active agent reservoir 202 from the power reservoir 201 and has a delivery nozzle 204 at the other end that is sealed with a pH responsive polymer to maintain the active agent integrity. The nozzle 204 will open at an intestinal site by dissolution of the pH responsive polymer at the relatively higher pH of the intestinal site (e.g., as compared to the stomach). Exterior to the power reservoir 201 of the active agent delivery device 200 is a heat reservoir 203, which contains food grade (94%-97%) anhydrous calcium chloride. The amount of anhydrous calcium chloride used is negligible as compared to the reported oral toxicity levels (e.g., oral dose of more than 2000 mg/kg is reported in the Material Safety Data Sheet for calcium chloride). The heat reservoir 203 has valves (e.g., holes) 205 on the outer wall, which are sealed with a pH responsive polymer and prevent the surrounding aqueous medium (e.g., water) from entering the heat reservoir 203 prior to the arrival of the active agent delivery device 200 to its target site (e.g., buccal or intestinal). Once the pH responsive valves 205 are dissolved at the target site, water from the oral cavity or intestine enters the heat reservoir 203. Water and anhydrous calcium chloride are brought into contact in the heat reservoir 203 and the heat that evolves from the dissolution of the calcium chloride heats the interior of the device, and thus heats the contents of the power reservoir 201. As a result of the rise in temperature (e.g., from 37° C. to 40° C.), the fluid mixture in the power reservoir 201 vaporizes and the hydraulic pressure on one side of the piston 206 increases. As shown in FIG. 2, panel C, the rise in pressure exerts a force on the piston 206, which moves the piston 206 in the manner of a plunger into the active agent reservoir 202 and the active agent formulation is then ejected from the nozzle 204 with high velocity. The active agent ejection power and velocity can be controlled by the amount of chemicals inside the power reservoir 201.

Example III

Device Activated by pH

Figure 3:
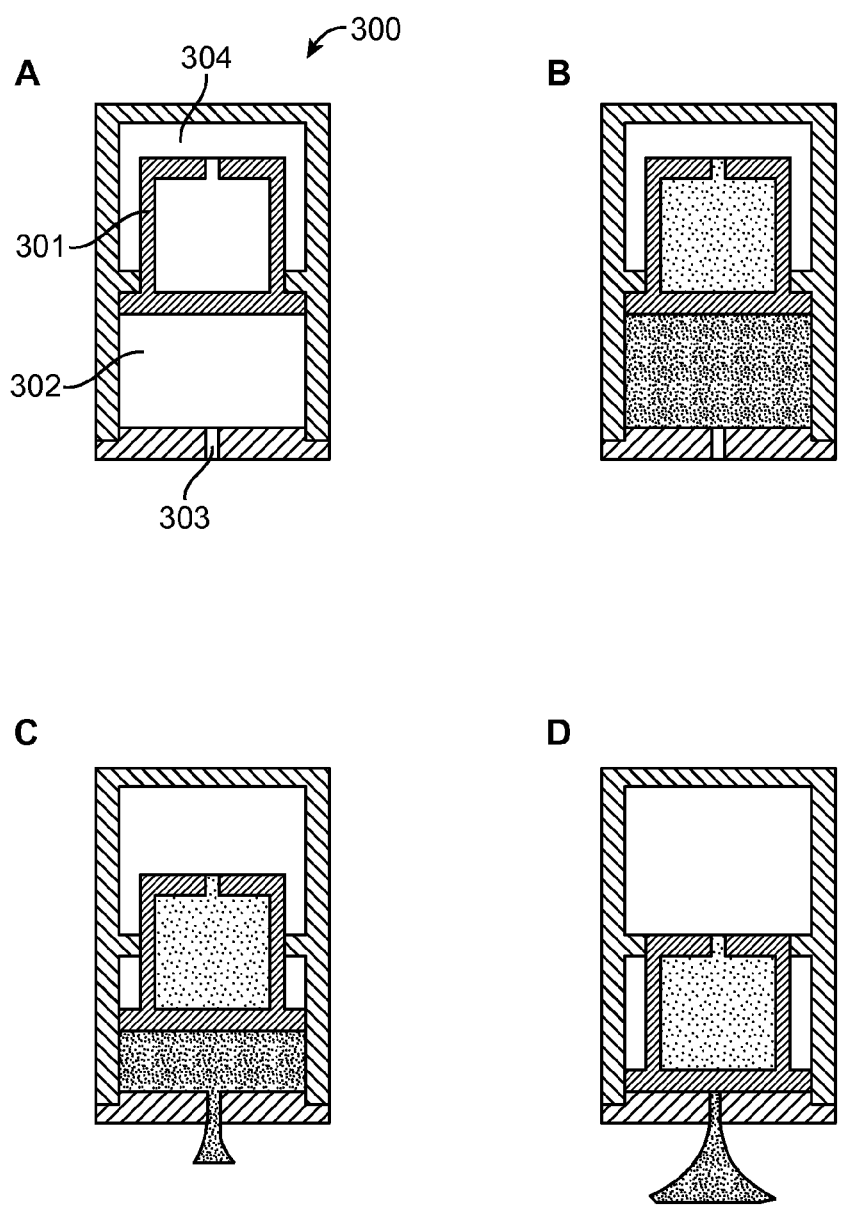
FIG. 3 provides views of an active agent delivery device where the power reservoir is included in the piston, according to embodiments of the present disclosure.

A schematic of an active agent delivery device 300 and its ejection mechanism is shown in FIG. 3. As shown in FIG. 3, panel A, the interior of the device 300 includes a movable piston 301 filled with a mixture of two chemicals (e.g., citric acid and sodium bicarbonate) in a powder form (e.g., the movable piston includes the power reservoir). The active agent reservoir 302 contains an active agent formulation and is sealed at one end by a freely movable guided piston 301 that separates the active agent reservoir 302 from the active agent formulation contained in the piston 301 and has a delivery nozzle 303 at the other end that is sealed with a pH responsive polymer to maintain the active agent integrity. The nozzle 303 will open at the target site by dissolution of the pH responsive polymer. The device 300 also includes a top reservoir 304 around the top portion of the piston 301 that contains pores on the outer wall, which are sealed with pH responsive polymer and prevent water from entering the top reservoir 304 of the device 300 prior to its arrival to the target site. Water and the contents of the piston 301 are brought into contact at the target site (e.g., the pH responsive polymer is designed to dissolve at the target site in response to the pH at the target site), which results in a chemical reaction and generation of carbon dioxide which increases the pressure inside the piston 301. As shown in FIG. 3, panel B, after administration of the device 300 and upon arrival at the target site, the pH responsive polymer covering the pores of the device's exterior dissolve, allowing the surrounding aqueous medium to enter the top reservoir 304. As shown in FIG. 3, panel C and panel D, carbon dioxide is generated when the aqueous medium contacts the contents of the piston 301, which exerts a hydraulic pressure on one side of the piston 301 and moves the piston 301 in the manner of a plunger into the active agent reservoir 302 and the active agent formulation in the active agent reservoir 301 is then ejected from the nozzle 303 with high velocity. The active agent ejection power and velocity can be controlled by the amount of chemicals inside the piston 301.

Example IV

Device Configured to have a Desired Active Agent Release Time

A schematic of an active agent delivery device 400 and its ejection mechanism is shown in FIG. 4. As shown in FIG. 4, panel A, the interior compartment of the device 400 includes two reservoirs separated by a membrane 409 and a movable piston 401. The active agent reservoir 402 is a sterile container that contains an active agent formulation and has a sealed delivery nozzle 403. The power reservoir 404 contains a dry mixture of citric acid and sodium bicarbonate which is sealed at one end by a separating region from the active agent reservoir 402 and is sealed with a pH responsive polymeric valve 405 at the other end. The pH responsive polymeric valve 405 can be designed to dissolve at a desired time (e.g., time, T) after exposure to a known amount of water (X amount of water or other solvent for the polymeric valve 405). The exterior compartment 406 of the device 400 includes a reservoir 407 filled with X amount of water (or other solvent) and is sealed with a thin membrane 408. As shown in FIG. 4, panel B, prior to administration of the device to the subject, the interior and the exterior compartments are attached together. This results in breakage of the thin membrane 408 sealing of the exterior compartment 407 and exposes the power reservoir 404 of the interior compartment to water. The polymeric valve 405 of the power reservoir 404 dissolves and after T time, allowing the dry power mixture inside the power reservoir 404 to absorb the water and trigger a chemical reaction, which generates a volume of $CO_2$ as a product. The hydraulic pressure increases inside the device, which breaks the separating membrane 409, and exerts a force on the piston 401, which moves the piston 401 in the manner of a plunger into the active agent reservoir 402, which will break a seal 410 on the nozzle 403 and the active agent formulation is then ejected from the nozzle 403 with high pressure.

Figure 13A:
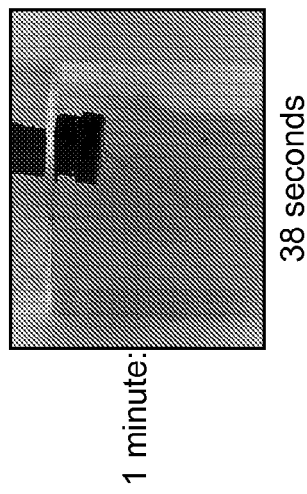
FIG. 13A shows a photograph of an active agent delivery device configured to release an active agent formulation in 1 min or less, according to embodiments of the present disclosure.
Figure 13B:
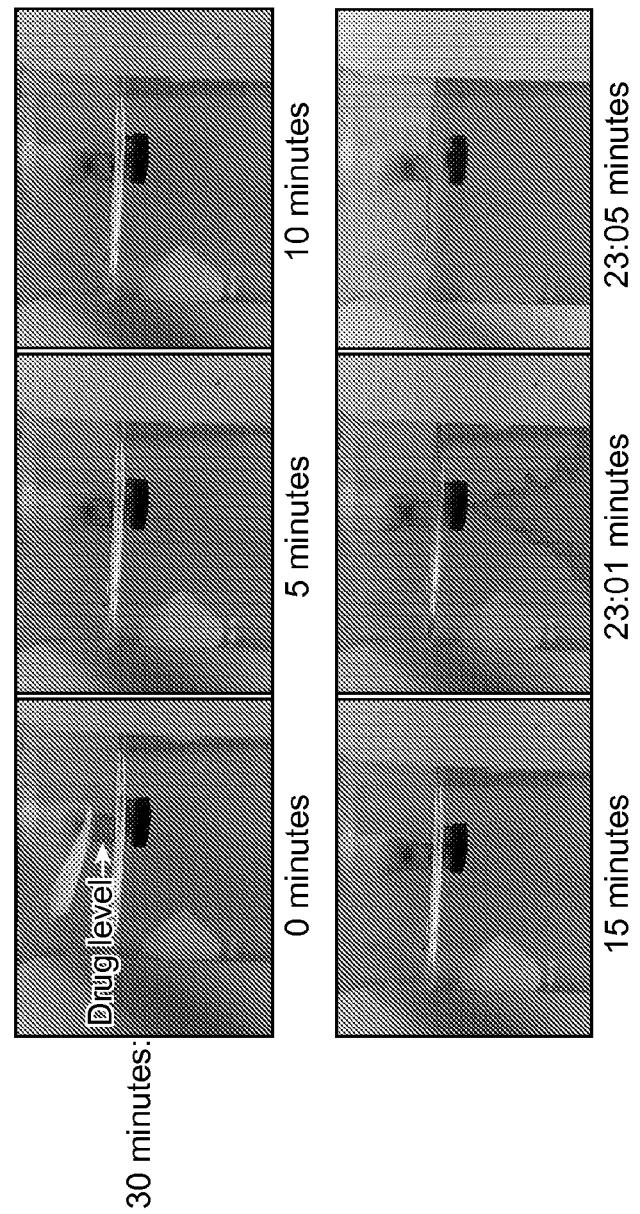
FIG. 13B shows photographs at various time points of an active agent delivery device configured to release an active agent formulation at about 23 minutes, according to embodiments of the present disclosure.
Figure 13C:
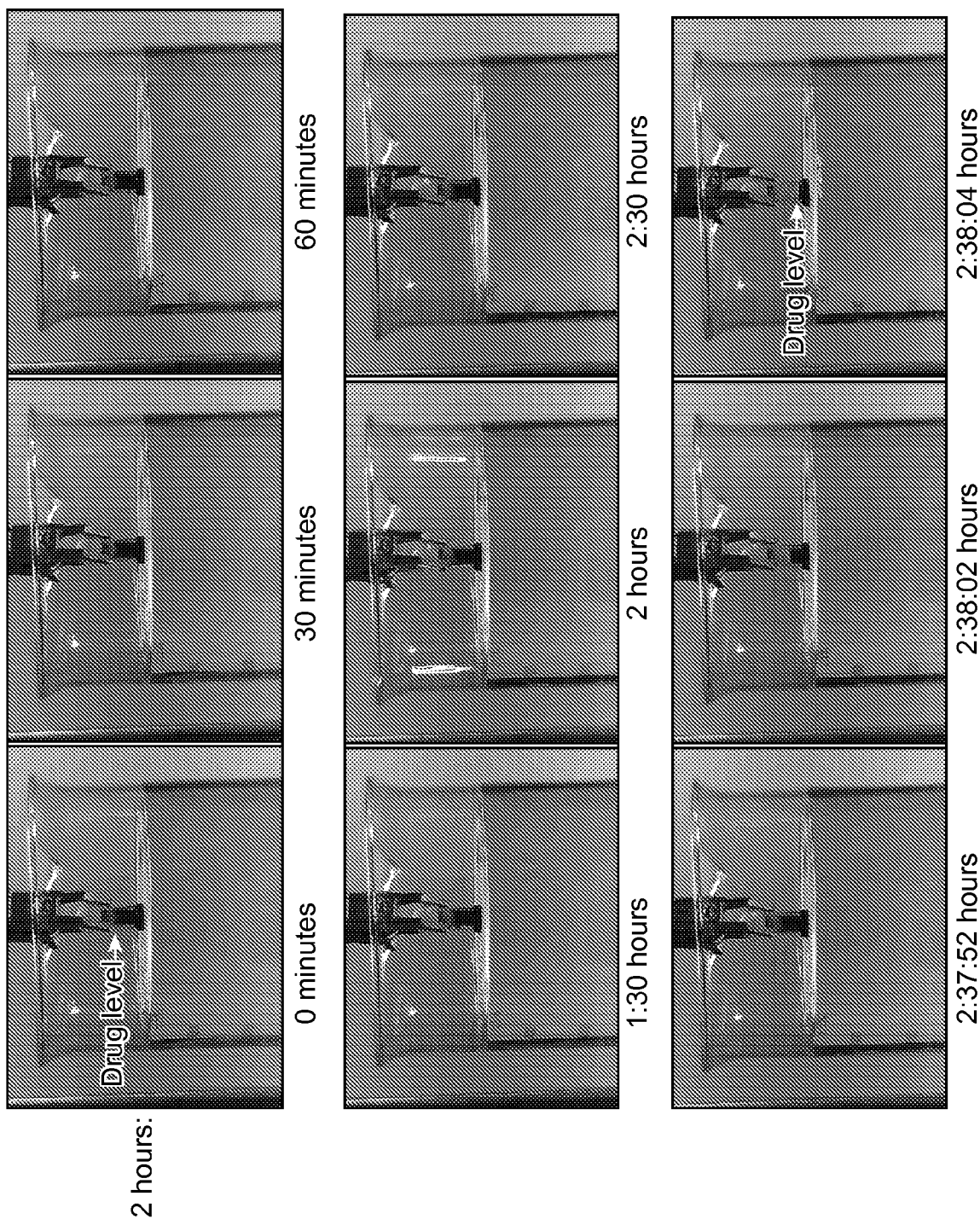
FIG. 13C shows photographs at various time points of an active agent delivery device configured to release an active agent formulation at about 2 hr and 30 min, according to embodiments of the present disclosure.

Experiments were performed utilizing an active agent delivery device of the present Example. The active agent delivery device included a polymeric valve surrounding a portion of the power reservoir (see, e.g., polymeric valve 405 illustrated in FIG. 4), which was a polymer designed to degrade after exposure to water after a desired amount of time (e.g., about 1 min, about 25 min, and about 2 hours and 30 min). The active agent delivery device was loaded with a hydrophilic dye in the active agent reservoir (e.g., to simulate an active agent formulation). The active agent delivery device and the exterior compartment were attached together and the activation time was recorded. FIG. 13A shows a photograph of an active agent delivery device 38 second after activation, which indicates activation in 38 second and complete release of the dye in less than 1 second. FIG. 13B shows photographs of a different device at various time points, which indicated activation at about 23 minutes. FIG. 13C shows photographs of a different device at various time points, which indicated activation at about 2 hr and 30 min (e.g., 2 hr 38 min). In all examples shown in FIGS. 13A-13C, the active agent formulation (e.g., dye) was released in less than 1 second. An active agent delivery device that releases the active agent formulation after a certain desired time period may facilitate a delayed release of the active agent formulation, such as a delayed release of the active agent formulation in an intestine of a subject at a certain desired time period after administration of the active agent delivery device to the subject.

Example V

Simulation Study to Evaluate the Effect of Pressure on Penetration Depth Through the Intestinal Wall Simulation results are shown in FIGS. 5A and 5B. The simulation was performed in ANSYS Fluent 15.0 using a 2D axisymmetric model with a transient (timestep of $10^{-4}$ s) pressure-based solver. An implicit volume of fluid model was used for multiphase modeling, and laminar flow was assumed. Three phases were modeled: chyme, mucus (with identical mechanical properties, modeled as different phases for visualization purposes), and active agent (modeled with the mechanical properties of water). Diffusion of active agent was ignored, which was justified due to the very high Peclet number of the system (~$10^7$, using Pe=UL/D with L=200 um, U=5 m/s from simulation, and D on the order of $10^{-6}$ cm$^2$/s). The mucus and chyme were modeled as non-Newtonian power law fluids, according to the equation:

$$\eta = k\dot{\gamma}^{n-1}$$

where the consistency index k=1.412 kg-s$^{n-2}$/m, the power-law index n=0.15, is the shear rate and is the viscosity. A maximum viscosity limit of 10 kg/m-s was used to prevent solution divergence in areas with zero shear rate. These parameters were taken from Cone (2009).

The mucus layer was assumed to be 200 μm thick based on published measurements of gastrointestinal mucus thickness (Atuma et al., 2001). A pressure boundary condition 1 cm away from the wall and 250 μm in diameter was used to simulate the ejection of the active agent from the device. Pressure data was taken from experiments and was curve fit using a 6$^{th}$-order polynomial fit in Microsoft Excel. The maximum pressure was 133 kPa, which decayed to ambient pressure (100 kPa). This was input as a time-dependent pressure boundary condition using an interpreted UDF written in C.

A number of simplifying assumptions were made in designing this model. The walls of the intestine were treated as rigid, immobile, and flat surfaces, ignoring the peristaltic motion of the intestine, the deformability of the intestinal wall, and the intestinal wall microstructure. Bulk flow in the intestine, which would occur in the direction perpendicular to the jet of released active agent, was also ignored. These assumptions were reasonable in light of the very short timescale of the active agent jet (reaching the wall within 5 milliseconds) and the comparatively small size of the microvilli when compared to the mucus layer. A simplified mechanical model of mucus and chyme was used, treating both as shear-thinning fluids rather than viscoelastic and spatially heterogeneous materials.

Simulations indicated that rapid, complete penetration of the mucus layer can occur within 5 ms (see FIG. 5A), even from 1 cm away from the wall (roughly half-way across the lumen of a typical human small intestine) with an overpressure at the device outlet of 33 kPa, which was attained using the devices of the present disclosure.

The pressure at the wall opposite the active agent jet origin reached 31 kPa overpressure within 3 ms (see FIG. 5B), demonstrating that little loss of pressure occurred during active agent jet penetration of the mucus layer. It has been shown that even small hydrodynamic pressure increases (on the order of hPa) enhance the permeability of endothelial cell layers (Tokuda, 2009), which should enhance absorption of active agent by the endothelium of the small intestine.

Calculation of wall shear stresses from the surface strain rates according to the shear stress equation for a power-law fluid gave wall shear stresses on the order of 10 Pa, which was well within physiological tolerances. The results indicated that the active agent delivery devices are safe to use without causing significant damage to the epithelium.

Example VI

In Vitro Delivery of Ovalbumin Across Pig Intestinal Tissue

The amount of ovalbumin delivered across intestinal tissue with and without using an active agent delivery device of the present disclosure is shown in FIG. 6.

For these studies, the lower wells of a Boyden chamber were filled with 3 mL of phosphate buffered saline (PBS) medium, millipore filters (pore size 0.2 μm) were inserted, and the whole assembly was placed onto a hot plate at 37° C. This was done to equilibrate the temperature of the mucosa slices and the chamber. Intestinal tissue was obtained from slaughtered domestic pigs. The tissue was kept in ice until isolation was done with a scalpel to an average thickness of 500±110 μm (n=3). Within 2 hrs of slaughter, the intestinal lumen was cut and the tissue was mounted on top of the filter with a forceps. The tissue covered the entire surface of the filter. 3 mL of medium at 37° C. was added to the upper well. The active agent delivery device was loaded with 400 μg of Alexa Fluor Ovalbumin (ovalbumin conjugated with fluorescent label) in 100 μL PBS, was held close to the intestinal tissue in the upper well and activated atop of the inner lumen of the small intestine in the upper chamber. For the control study, the same amount of Alexa Fluor Ovalbumin (400 μg in 100 μL) was deposited into the upper chamber using a dropper). 50 μL of solution from the lower well was collected every 15 minutes to study the kinetics of Ova-Alexa delivery across intestinal membrane. For the control study, the same amount of Ova-Alexa was placed atop intestinal tissue utilizing a dropper (FIG. 6). As indicated in FIG. 6, the active agent delivery device enhanced intestinal absorption of ovalbumin as compared to diffusion only.

Example VII

In Vitro Delivery of Ovalbumin Across Pig's Buccal Membrane Tissue

The amount of ovalbumin delivered across buccal tissue with and without utilizing an active agent delivery device of the present disclosure is shown in FIG. 7.

For these studies, the lower wells of a Boyden chamber were filled with 3 mL of PBS medium, millipore filters (pore size 0.2 μm) were inserted, and the whole assembly was placed onto a hot plate at 37° C. This was done to equilibrate the temperature of the mucosa slices and the chamber. buccal tissue (cheeks) was obtained from slaughtered domestic pigs. The tissue was kept in ice until isolation was done with a scalpel to obtain buccal tissue (average thickness of 500±110 μm) (n=3). Within 2 hrs of slaughter, the tissue was mounted on top of the filter with a forceps. The tissue covered the entire surface of the filter. 3 mL of medium at 37° C. was added to the upper well. The active agent delivery device was loaded with 400 μg of Alexa Fluor Ovalbumin (ovalbumin conjugated with fluorescent label) in 100 μL PBS, was held close to the buccal tissue in the upper well and activated in the upper chamber. For the control study, the same amount of Alexa Fluor Ovalbumin (400 μg in 100 μL) was deposited into the upper chamber using a dropper. 50 μL of solution from the lower well was collected every 15 minutes to study the kinetics of Ova-Alexa delivery across buccal membrane. For the control study, the same amount of Ova-Alexa was placed atop intestinal tissue utilizing a dropper (FIG. 7). As indicated in FIG. 7, the active agent delivery device (pressure-based delivery) enhanced buccal absorption of ovalbumin as compared to diffusion only.

Example VIII

In-Vivo Buccal Delivery of Ovalbumin for Oral Vaccination Using a Device of Example IV Antibody response after buccal vaccination using an active agent delivery device of the present disclosure loaded with ovalbumin. Rabbits were immunized two times (week 0 and after blood collection at week 4) by placing the device inside the rabbits cheeks and against the buccal tissue. Serum was collected on weeks 0, 1, 2, 3, 4, 5 and 6. For tissue IgG analysis, mucosal tissue (buccal tissue, lymph nodes and payer's patches) were collected after the animals were euthanized at week 6 for IgA analysis. ELISA results were reported as optical density (OD) at 450 nm (see FIGS. 8A and 8B).

All procedures were conducted in accordance with protocols approved by the University of California Berkeley Committee on Animal Care. Ovalbumin was chosen as a model biologic vaccine because large proteins such as ovalbumin have negligible oral bioavailability and ovalbumin is a common vaccine model. In vivo rabbit studies were performed on six New Zealand white rabbits weighing approximately 2.5-3.5 kg. Prior to the procedures, the animals were sedated for calm and comfort with subcutaneous administration of 1 mg/kg acepromazine for animal sedation and comfort. After sedation, for experimental studies, the active agent delivery device was loaded with a solution of ovalbumin (100 µg/Kg) and was held against the buccal tissue using a pill holder. Prior to device administration, 200 µL of blood samples were taken from marginal ear vein to quantify the animal's starting blood-anti-ova immunoglobulin G (IgG) levels. After device activation (time=~1-2 min) and ovalbumin delivery the device was removed from the oral cavity. The rabbits were then placed back in the cage. Blood samples were then taken weekly for 6 weeks. Plasma was separated by centrifugation and was stored at 80° C. until analyzed. At week 4, a booster dose of 100 µg/kg ovalbumin in sterile PBS was given to rabbits using a similar method. Control rabbits received the same amount of ovalbumin using a dropper against the buccal tissue. To evaluate the levels of anti-ovalbumin IgG antibodies, ELISA was performed on blood serum. To evaluate anti-ovalbumin IgA antibodies (mucosal IgA) analysis 100 mg tissue was rinsed with 1× PBS, homogenized in 1 mL of 1×PBS and stored overnight at −20° C. After two freeze-thaw cycles were performed to break the cell membranes, the homogenates were centrifuged for 5 minutes at 5000×g. The supernate was removed immediately and ELISA was performed to monitor IgA levels in buccal tissue, payer's patches and lymph nodes.

Control rabbits received the same amount of ovalbumin using a dropper against the buccal tissue.

Figure 8A:
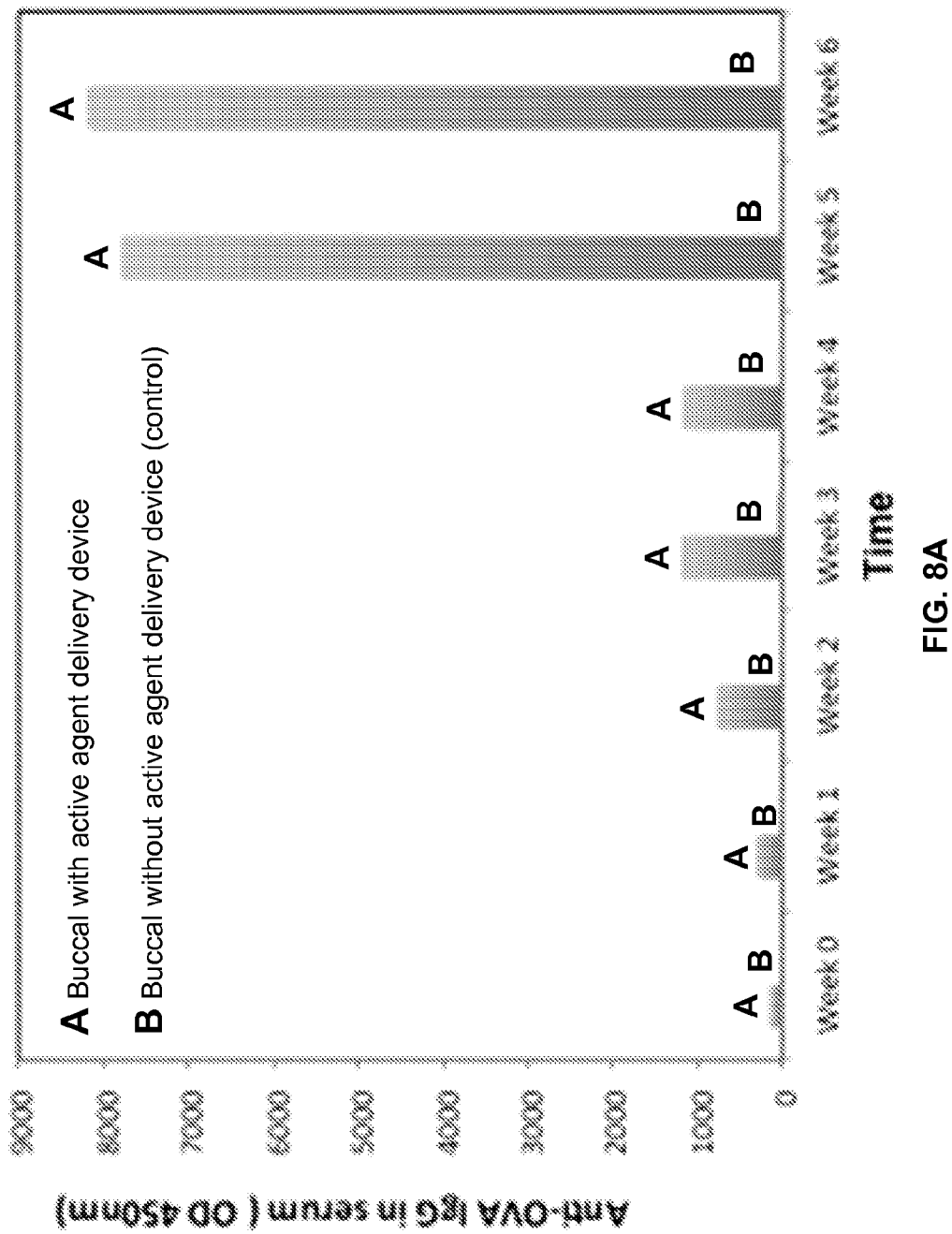
FIG. 8A provides a graph of the in vivo results from rabbit buccal vaccination against ovalbumin (OVA) with and without using a device of the present disclosure in New Zealand white rabbits. The graph shows blood anti-OVA IgG levels in serum over a 6 week experimental period, which shows the antibody response after buccal vaccination using a device of the present disclosure loaded with ovalbumin. Rabbits were immunized two times (week 0 and after blood collection at week 4) by placing the device inside the rabbits' cheeks and against the buccal tissue. Serum was collected on weeks 0, 1, 2, 3, 4, 5 and 6. ELISA results are reported as optical density (OD) at 450 nm.

FIG. 8A provides a graph of the in vivo results from New Zealand white rabbit buccal vaccination against ovalbumin (OVA) with and without using a device of Example IV above. As shown in FIG. 8A, there was no significant antibody serum response after the control vaccination (i.e., without using an active agent delivery device). However, vaccination using an active agent delivery device produced a significant serum antibody response.

Figure 8B:
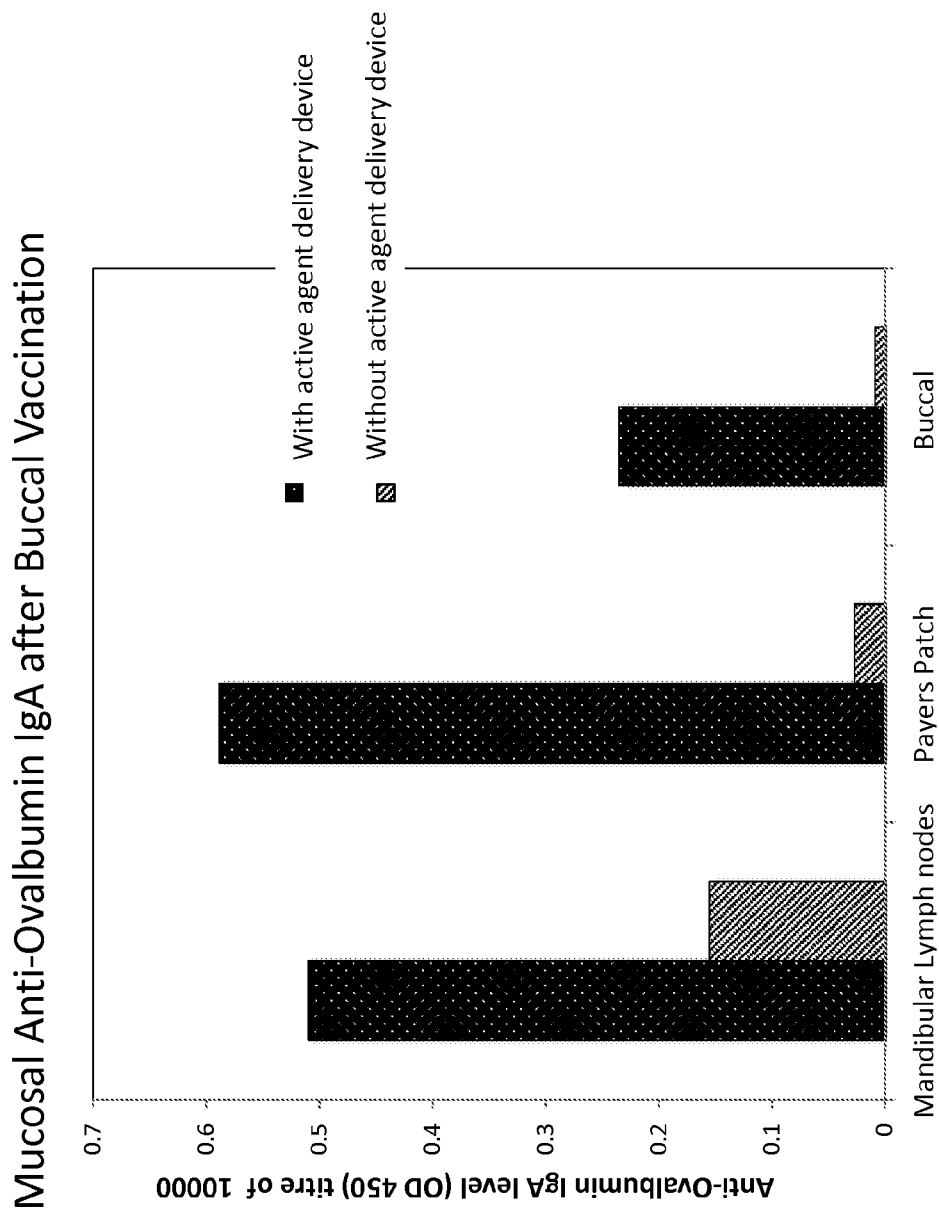
FIG. 8B provides a graph of the in vivo results from New Zealand white rabbit buccal vaccination against ovalbumin (OVA) with and without using a device of the present disclosure. The graph shows the tissue anti-OVA IgA level.

FIG. 8B provides a graph of the in vivo results from New Zealand white rabbit buccal vaccination against ovalbumin (OVA) with and without using a device of the present disclosure. The graph in FIG. 8B shows the tissue anti-OVA IgA level. As shown in FIG. 8B, the antibody responses in the lymph node, payer's patch and buccal tissues were significantly higher after vaccination using the active agent delivery device as compared to the control.

The results for the experiments indicated that device (pressure-based) delivery to the buccal area was able to activate the immune response effectively without the need for adjuvant. In addition, the production of Ova-specific IgA antibody in mucosal tissues and payer's patches indicated that device delivery to buccal area was superior to the intramuscular route by inducing mucosal immunity.

Example IX

Device Activated by pH

Figure 9:
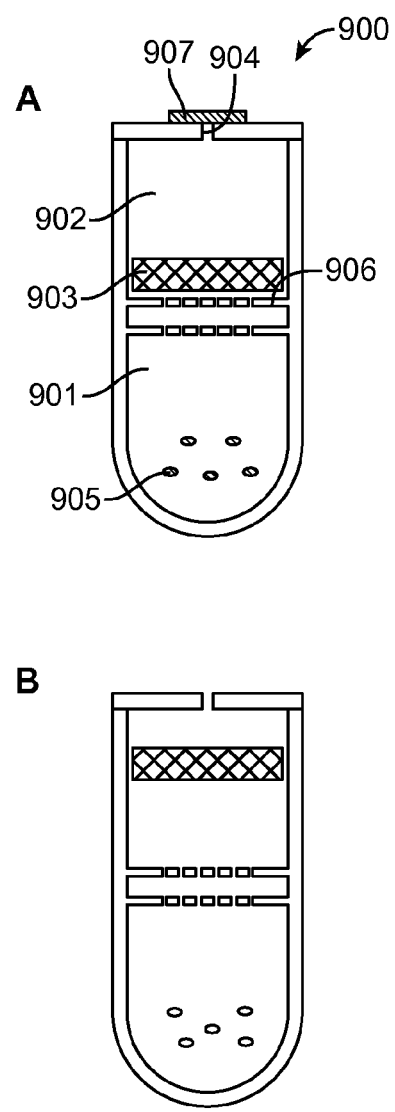
FIG. 9 provides views of an active agent delivery device where the device is activated by a change in pH, according to embodiments of the present disclosure.

A schematic of an active agent delivery device 900 is shown in FIG. 9, where the active agent delivery device is activated by pH. As shown in FIG. 9, panel A, the active agent delivery device 900 includes two reservoirs, the power reservoir 901 and the active agent reservoir 902, separated by a movable separator (i.e., a movable piston) 903. The power reservoir 901 contains a mixture of chemicals (citric acid and sodium bicarbonate) in a powder form and is also separated from the active agent reservoir by a membrane 906. The active agent delivery device 900 is administered to a subject orally. Upon arrival at the intestinal site, the active agent delivery device 900 is activated and $CO_2$ is generated inside the power reservoir 901, which increases the pressure inside the power reservoir 901. Activation of the contents of the power reservoir 901 occurs when the aqueous medium at the intestinal site enters into the power reservoir 901 through one or more valves 905 in the power reservoir 901. Each valve 905 includes a hole in the wall of the power reservoir 901, and also includes a pH sensitive material. Upon contact of the pH sensitive material with the relatively higher pH in the intestinal site (e.g., as compared to the stomach) the pH sensitive material can degrade, thus opening the hole in the wall of the power reservoir for entry of the surrounding aqueous medium into the power reservoir 901. As shown in FIG. 9, panel B, the increase in pressure exerts a force on the piston 903, which moves the piston 903 into the active agent reservoir 902, which will break a seal 907 on the nozzle 904 and the active agent solution is then ejected from the nozzle 904 with high velocity.

Example X

Device Activated by Temperature and pH

Figure 10:
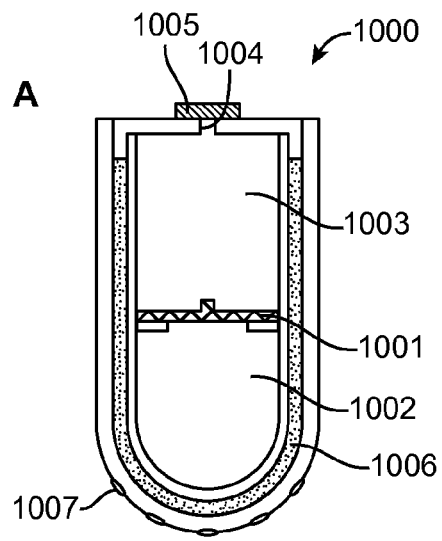
FIG. 10 provides views of an active agent delivery device where the device is activated by temperature, according to embodiments of the present disclosure.
Figure 10:
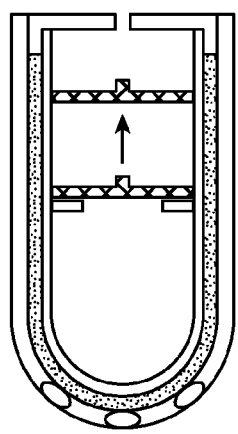

A schematic of an active agent delivery device 1000 and its ejection mechanism is shown in FIG. 10, where the active agent delivery device is activated by temperature and pH. As shown in FIG. 10, panel A, the interior of the active agent delivery device 1000 includes two reservoirs separated by a movable piston 1001. The power reservoir 1002 contains a liquid with a vaporization temperature greater than normal body temperature (e.g., 40° C.). The active agent reservoir 1003 contains an active agent and is sealed at one end by a freely movable guided piston 1001 that separates the active agent reservoir 1003 from the power reservoir 1002 and has a delivery nozzle 1004 at the other end that is sealed with a pH responsive polymer 1005 to maintain the active agent integrity. The nozzle 1004 will open at an intestinal site by dissolution of the pH responsive polymer 1005 at the relatively higher pH of the intestinal site (e.g., as compared to the stomach). Exterior to the power reservoir 1002 of the active agent delivery device 1000 is a heat reservoir 1006, which contains a composition that can generate heat upon contact with an aqueous medium (e.g., anhydrous calcium chloride). The heat reservoir 1006 has valves (e.g., holes) 1007 on the outer wall, which are sealed with a pH responsive polymer and prevent the surrounding aqueous medium (e.g., water) from entering the heat reservoir 1006 prior to the arrival of the active agent delivery device 1000 to its target site (e.g., intestinal). Once the pH responsive valves 1007 are dissolved at the target site, the surrounding aqueous medium (e.g., water) from the intestine enters the heat reservoir 1006, thus causing the heat generating material in the heat reservoir 1006 to generate heat, which in turn heats the contents of the power reservoir 1002. As a result of the rise in temperature (e.g., from 37° C. to 40° C.), the fluid mixture in the power reservoir 1002 vaporizes and the hydraulic pressure on one side of the piston 1001 increases. As shown in FIG. 10, panel B, the rise in pressure exerts a force on the piston 1001, which moves the piston 206 in the manner of a plunger into the active agent reservoir 202 and the active agent formulation is then ejected from the nozzle 1004 with high velocity.

Example XI

Self-Contained Device

A schematic of a self-contained active agent delivery device 1100 and its ejection mechanism is shown in FIG. 11. As shown in FIG. 11, panel A, the interior compartment of the device 1100 includes a power reservoir 1004 and an active agent reservoir 1102 separated by a membrane 1109 and a movable piston 1101. The active agent reservoir 1102 is a sterile container that contains an active agent formulation and has one or more sealed delivery nozzles 1103. The power reservoir 1104 contains a pressure generating material (e.g., a gas generating material, such as a dry mixture of citric acid and sodium bicarbonate), which is sealed at one end by membrane 1109 from the active agent reservoir 1102 and is sealed with a frangible valve 1105 at the other end. The device 1100 also includes an aqueous medium reservoir 1107 filled with an aqueous medium. As shown in FIG. 11, panel B, during use of the device, a plunger 1108 attached to one or more puncturing elements 1110 can be depressed, which results in breakage of the frangible valve 1105 sealing the aqueous medium reservoir 1107 and thus exposes the power reservoir 1104 to the aqueous medium contained in the aqueous medium reservoir 1107. This allows the gas generating material inside the power reservoir 1104 to activate and trigger a chemical reaction, which generates a volume of gas as a product. The hydraulic pressure increases inside the device, which exerts a force on the piston 1101, which moves the piston 1101 in the manner of a plunger into the active agent reservoir 1012, which will break a seal 1111 on the nozzle 1103 and the active agent formulation is then ejected from the nozzle 1103 with high pressure.

FIG. 11, panel C shows an alternative embodiment of an active agent delivery device, where the nozzle 1150 extends from a side wall of the active agent reservoir 1151. A nozzle that extends from a side wall of the device (e.g., extend from a side wall of the active agent reservoir) can facilitate delivery of the active agent to a mucosal layer positioned alongside of the device, such as in a nasal cavity.

Example XII

Low-Profile Device

Figure 12:
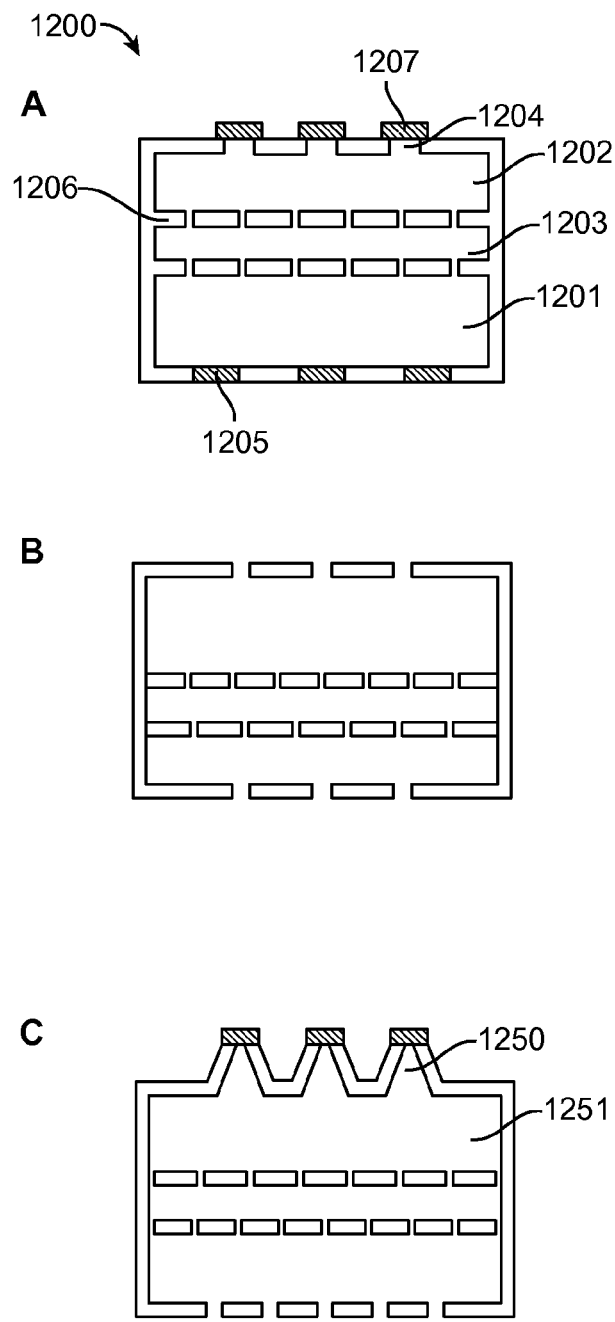
FIG. 12 provides views of an active agent delivery device where the device is activated by a gas generating chemical reaction, according to embodiments of the present disclosure.

A schematic of a low-profile active agent delivery device 1200 is shown in FIG. 12. As shown in FIG. 12, panel A, the active agent delivery device 1200 includes two reservoirs, the power reservoir 1201 and the active agent reservoir 1202, separated by a gap (e.g., air space) 1203. The power reservoir 1201 contains a pressure generating material (e.g., a gas generating material) and is separated from the active agent reservoir by one or more membranes 1206. The low-profile active agent delivery device 1200 can be applied to a mucosal surface in a subject, such as applied to a buccal surface. Activation of the contents of the power reservoir 1201 occurs, for example when an aqueous medium at the administration site enters into the power reservoir 1201 through one or more valves 1205 in the power reservoir 1201. Each valve 1205 includes a hole the wall of the power reservoir 1201, and also includes a dissolvable material. Upon application to the mucosal surface, the dissolvable material can degrade, thus opening the valve 1205 of the power reservoir for entry of the surrounding aqueous medium into the power reservoir 1201. As shown in FIG. 12, panel B, an increase in pressure in the power reservoir 1201 due to activation of the pressure generating material exerts a force on the active agent reservoir 1202, which will break a seal 1207 on the nozzle 1204 and the active agent solution is then ejected from the nozzle 1204 with high velocity.

FIG. 12, panel C shows an alternative embodiment of a low-profile active agent delivery device, where the nozzles 1250 protrude from a surface of the active agent reservoir 1251. The nozzles can have a shape of a cone or frustum, and can facilitate delivery of the active agent into and/or through a mucosal layer upon which the device is applied.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. An active agent delivery device comprising:
an active agent reservoir at an active agent reservoir end of the device configured to contain an active agent formulation;
a power reservoir at a power reservoir end of the device configured to eject the active agent formulation at a pressure sufficient to deliver the active agent formulation into or through a mucosal layer in a subject, wherein the power reservoir comprises one or more valves, wherein the one or more valves separates the power reservoir from the exterior of the device, wherein the one or more valves comprises a pH responsive material and is configured to degrade or dissolve and thereby provide an inlet into the power reservoir in response to a change in pH; and
a moveable separator separating the power reservoir from the active agent reservoir.

2. The active agent delivery device of claim 1, wherein the pressure generated by the device is 30 kPa or more.

3. The active agent delivery device of claim 1, wherein the active agent formulation is ejected from the device in 10 msec or less.

4. The active agent delivery device of claim 1, wherein the active agent formulation is ejected from the device at a velocity of 1 m/s or more.

5. The active agent delivery device of claim 1, wherein the device comprises a nozzle separating the active agent reservoir from the exterior of the device.

6. The active agent delivery device of claim 1, wherein the power reservoir contains a gas generating material.

7. The active agent delivery device of claim 6, wherein the gas generating material produces a gas upon contact with an aqueous medium.

8. The active agent delivery device of claim 7, wherein the gas is a product of a chemical reaction.

9. The active agent delivery device of claim 6, wherein the gas generating material is a volatile liquid.

10. The active agent delivery device of claim 9, wherein the volatile liquid has a vaporization temperature ranging from 37.5° C. to 45° C.

11. The active agent delivery device of claim 1, wherein the moveable separator contains a gas generating material.

12. The active agent delivery device of claim 9, wherein the device comprises a heat reservoir in heat transfer relationship with the power reservoir, wherein the heat reservoir comprises a heat generating material that produces heat upon contact with an aqueous medium.

13. The active agent delivery device of claim 1, wherein the pH responsive material comprises a polymer.

14. The active agent delivery device of claim 1, wherein the device further comprises an aqueous medium reservoir configured to contact at least a portion of the power reservoir end of the device and activate the power reservoir.

15. The active agent delivery device of claim 14, wherein the power reservoir contains a gas generating material and the aqueous medium reservoir contains an aqueous medium.

16. The active agent delivery device of claim 1, wherein the active agent comprises a macromolecule.

17. The active agent delivery device of claim 16, wherein the macromolecule comprises a protein.

18. The active agent delivery device of claim 1, wherein the active agent formulation comprises a liquid.

19. The active agent delivery device of claim 1, wherein the device comprises a tubular member having a planar surface at the active agent reservoir end and a hemispherical structure at the power reservoir end.

20. The active agent delivery device of claim 1, wherein the device is configured to promote contact of the active agent reservoir end with a mucosal surface in a subject.

21. A method of delivering an active agent to a subject, wherein the method comprises administering an active agent delivery device of claim 1 to a subject.

22. The method of claim 21, wherein the method is a method of treating the subject for a disease condition.

23. A kit comprising:
an active agent delivery device of claim 1; and
a packaging containing the active agent delivery device.

24. The kit of claim 23, wherein the packaging contains two or more of the active agent delivery devices.

25. The kit of claim 23, further comprising a mucosal treatment agent.

26. The active agent delivery device of claim 1, wherein the one or more valves includes one or more holes and a pH responsive material.

27. The active agent delivery device of claim 1, wherein the one or more valves comprises a hole in the wall of the power reservoir.

28. The active agent delivery device of claim 1, wherein the one or more valves degrade or dissolve at a pH of 4 or less.

29. The active agent delivery device of claim 1, wherein the one or more valves degrade or dissolve at a pH of 5 or more.

* * * * *